(12) United States Patent
Koike et al.

(10) Patent No.: US 8,466,166 B2
(45) Date of Patent: Jun. 18, 2013

(54) BENZIMIDAZOLE DERIVATIVES AS SELECTIVE ACID PUMP INHIBITORS

(75) Inventors: Hiroki Koike, Aichi-ken (JP); Mikio Morita, Aichi-ken (JP)

(73) Assignee: Raqualia Pharma Inc., Aichi-Ken (JP)

( * ) Notice: Subject to any disclaimer, the term of this patent is extended or adjusted under 35 U.S.C. 154(b) by 507 days.

(21) Appl. No.: 12/442,277

(22) PCT Filed: Sep. 17, 2007

(86) PCT No.: PCT/IB2007/002749
§ 371 (c)(1),
(2), (4) Date: Mar. 20, 2009

(87) PCT Pub. No.: WO2008/035195
PCT Pub. Date: Mar. 27, 2008

(65) Prior Publication Data
US 2010/0048532 A1    Feb. 25, 2010

Related U.S. Application Data

(60) Provisional application No. 60/826,442, filed on Sep. 21, 2006, provisional application No. 60/912,264, filed on Apr. 17, 2007.

(51) Int. Cl.
*A61K 31/44* (2006.01)
*A61K 31/445* (2006.01)
*A61K 31/41* (2006.01)

(52) U.S. Cl.
USPC ........... 514/279; 514/292; 514/321; 514/326; 514/337; 514/360

(58) Field of Classification Search
USPC ................ 514/279, 292, 321, 326, 337, 360
See application file for complete search history.

(56) References Cited

U.S. PATENT DOCUMENTS 6,106,864 A    8/2000   Dolan et al.

FOREIGN PATENT DOCUMENTS

| WO | WO 91/11172 | 8/1991 |
|---|---|---|
| WO | WO 94/02518 | 2/1994 |
| WO | WO 98/55148 | 12/1998 |
| WO | WO 99/40091 | 8/1999 |
| WO | WO 00/35298 | 6/2000 |
| WO | WO 2004/054984 A1 | 7/2004 |
| WO | WO 2004/087701 A1 | 10/2004 |
| WO | WO 2006/037759 A1 | 4/2006 |
| WO | WO 2006/100255 A1 | 9/2006 |
| WO | WO 2006/136552 A2 | 12/2006 |

OTHER PUBLICATIONS

Hirschowitz B.I. et al., "Pharmacological Aspects of Acid Secretion", *Digestive Diseases and Sciences* 40(2):3S-23S (1995).

Sachs G. et al., "The Pharmacology of the Gastric Acid Pump: The $H^+$, $K^+$ ATPase[1,2]", *Annu. Rev. Pharmacol. Toxicol.* 35:277-305 (1995).

Pope A.J. et al., "Reversible Inhibitors of the Gastric $H^+/K^+$-Transporting ATPase: a New Class of Anti-Secretory Agent", *Trends in Pharmacological Sciences* 14:323-325 (1993).

Vakil N., "Review Article: New Pharmacological Agents for the Treatment of Gastro-Oesophageal Reflux Disease", *Aliment Pharmacol Ther.* 19:1041-1049 (2004).

Kiljander T.O., "The Role of Proton Pump Inhibitors in the Management of Gastroesophageal Reflux Disease-Related Asthma and Chronic Cough", *The American Journal of Medicine* 115(3A):65S-71S (2003).

Yeo M. et al., "The Novel Acid Pump Antagonists for Anti-Secretory Actions With Their Peculiar Applications Beyond Acid Suppression", *J. Clin. Biochem. Nutr.* 38:1-8 (2006).

Stahl P.H. et al., "Handbook of Pharmaceutical Salts: Properties, Selection, and Use", (Wiley-VCH, Weinheim, Germany, 2002), 4 pages.

Haleblian J.K., "Characterization of Habits and Crystalline Modification of Solids and Their Pharmaceutical Applications", *Journal of Pharmaceutical Sciences* 64(8):1269-1288 (1975).

Greene T.W. et al., "Protective Groups in Organic Synthesis", (John Wiley & Sons, 1999), pp. 17-247.

Sawamura M. et al., "The Asymmetric Aldol Reaction of Tosylmethyl Isocyanide and Aldehydes Catalyzed by Chiral Silver(I) Complexes", *J. Org. Chem.* 55:5935-5936 (1990).

(Continued)

*Primary Examiner* — Renee Claytor
(74) *Attorney, Agent, or Firm* — Scully, Scott, Murphy & Presser, P.C.

(57) ABSTRACT

This invention relates to compounds of the formula (I): or a pharmaceutically acceptable salt thereof, wherein: $R^1$, $R^2$, $R^3$, $R^4$, A and E are each as described herein or a pharmaceutically acceptable salt, and compositions containing such compounds and the method of treatment and the use, comprising such compounds for the treatment of a condition mediated by acid pump antagonistic activity such as, but not limited to, as gastrointestinal disease, gastroesophageal disease, gastroesophageal reflux disease (GERD), laryngopharyngeal reflux disease, peptic ulcer, gastric ulcer, duodenal ulcer, NSAID-induced ulcers, gastritis, infection of *Helicobacter pylori*, dyspepsia, functional dyspepsia, Zollinger-Ellison syndrome, non-erosive reflux disease (NERD), visceral pain, cancer, heartburn, nausea, esophagitis, dysphagia, hypersalivation, airway disorders or asthma.

(I)

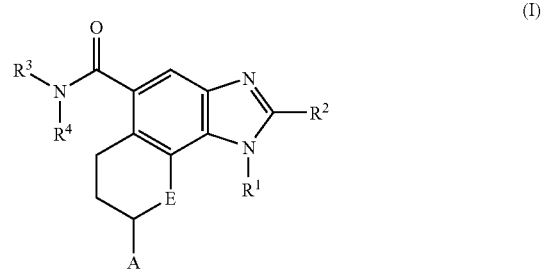

8 Claims, No Drawings

OTHER PUBLICATIONS

Yang D. et al,, "Local and Framework Stereochemical Markers in Vibrational Circular Dichroism: 1,2- and 2,3-Dimethylaziridines", *Canadian Journal of Chemistry* 71:2028-2037 (1993).

Lee N.E. et al., "Asymmetric Hydrogenation of Enamines With a Chiral Titanocene Catalyst", *J. Am. Chem. Soc. 116*:5985-5986 (1994).

Greene T.W. et al., "Protective Groups in Organic Synthesis", pp. 369-453 (1999).

'Remington's Pharmaceutical Sciences', 19$^{th}$ Edition (Mack Publishing Company, 1995).

Liang A.C. et al., "Fast-Dissolving Intraoral Drug Delivery Systems", *Expert Opinion in Therapeutic Patents 11*(6):981-986 (2001).

"Pharmaceutical Dosage Forms: Tablets, vol. 1", by H. Lieberman and L. Lachman, Marcel Dekker, N.Y., N.Y., 1980 (ISBN 0-8247-6918-X).

Verma R.K. et al., "Current Status of Drug Delivery Technologies and Future Directions", *Pharmaceutical Technology On-Line 25*(2):1-14 (2001).

Firmin B.C. et al., "Transdermal Penetration Enhancers: Applications, Limitations, and Potential", *Journal of Pharmaceutical Sciences 88*(10):955-958 (1999).

Keeling D.J. et al., "SCH 28080 is a Lumenally Acting $K^+$-Site Inhibitor of the Gastric ($H^+$+$K^+$)-ATPase", *Biochemical Pharmacology 37*(11):2231-2236 (1988).

Watanabe K. et al., "Stimulation of Gastric Acid Secretion by Progesterone Metabolites as Neuroactive Steroids in Anesthetized Rats", *J. Physiol.* (Paris) 94:111-116 (2000).

Heidenhain R., "Ueber Die Absonderug Der Fundusdrüsen Des Magens", *Arch. Ges. Physiol. 19*:148-167 (1879).

Zhou Z. et al., "Properties of HERG Channels Stably Expressed in HEK 293 Cells Studied at Physiological Temperature", *Biophysical Journal* 74:230-241 (1998).

BENZIMIDAZOLE DERIVATIVES AS SELECTIVE ACID PUMP INHIBITORS

BACKGROUND OF THE INVENTION

This invention relates to tricyclic compounds. These compounds have selective acid pump inhibitory activity. The present invention also relates to a pharmaceutical composition, method of treatment and use, comprising the above derivatives for the treatment of disease conditions mediated by acid pump modulating activity; in particular acid pump inhibitory activity.

It has been well established that proton pump inhibitors (PPIs) are prodrugs that undergo an acid-catalyzed chemical rearrangement that permits them to inhibit $H^+/K^+$-ATPase by covalently binding to its Cystein residues (Sachs, G. et. al., *Digestive Diseases and Sciences*, 1995, 40, 3S-23S; Sachs et al., *Annu Rev Pharmacol Toxicol*, 1995, 35, 277-305.). However, unlike PPIs, acid pump antagonists inhibit acid secretion via reversible potassium-competitive inhibition of $H^+/K^+$-ATPase. SCH28080 is one of such reversible inhibitors and has been studied extensively. Other newer agents (revaprazan, soraprazan, AZD-0865 and CS-526) have entered in clinical trials confirming their efficacy in human (Pope, A.; Parsons, M., *Trends in Pharmacological Sciences*, 1993, 14, 323-5; Vakil, N., *Alimentary Pharmacology and Therapeutics*, 2004, 19, 1041-1049.). In general, acid pump antagonists are found to be useful for the treatment of a variety of diseases, including gastrointestinal disease, gastroesophageal disease, gastroesophageal reflux disease (GERD), laryngopharyngeal reflux disease, peptic ulcer, gastric ulcer, duodenal ulcer, non-steroidal anti-inflammatory drug (NSAID)-induced ulcers, gastritis, infection of *Helicobacter pylori*, dyspepsia, functional dyspepsia, Zollinger-Ellison syndrome, non-erosive reflux disease (NERD), visceral pain, cancer, heartburn, nausea, esophagitis, dysphagia, hypersalivation, airway disorders or asthma (hereinafter, referred as "APA Diseases"; Kiljander, Toni O, *American Journal of Medicine*, 2003, 115 (Suppl. 3A), 65S-71S; Ki-Baik Hahm et al., *J. Clin. Biochem. Nutr.*, 2006, 38, (1), 1-8.).

WO04/87701 refers to some compounds, such as tricyclic benzimidazole derivatives, as acid pump antagonists.

There is a need to provide new acid pump antagonists that are good drug candidates and address unmet needs by PPIs for treating diseases. In particular, preferred compounds should bind potently to the acid pump whilst showing little affinity for other receptors and show functional activity as inhibitors of acid-secretion in stomach. They should be well absorbed from the gastrointestinal tract, be metabolically stable and possess favorable pharmacokinetic properties. They should be non-toxic. Furthermore, the ideal drug candidate will exist in a physical form that is stable, non-hygroscopic and easily formulated.

SUMMARY OF THE INVENTION

In this invention, it has now been found out that the new class of tricyclic compounds having a substituted alkyl group at 1 position show acid pump inhibitory activity and good bioavailability as drug candidates, and thus are useful for the treatment of disease conditions mediated by acid pump inhibitory activity such as APA Diseases.

The present invention provides a compound of the following formula (I):

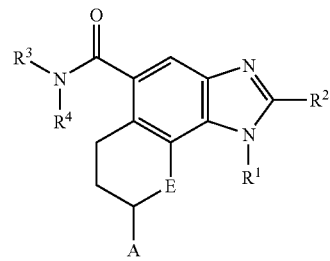

or a pharmaceutically acceptable salt thereof, wherein;

$R^1$ represents a $C_1$-$C_6$ alkyl group being unsubstituted or substituted with 1 to 2 substituents independently selected from the group consisting of a hydroxy group, a $C_1$-$C_6$ alkoxy group, a hydroxy-substituted $C_3$-$C_7$ cycloalkyl group, a hydroxy-$C_1$-$C_6$ alkyl-substituted $C_3$-$C_7$ cycloalkyl group, an aryl group, a hydroxy-substituted aryl group, a heteroaryl group and a halogen-substituted heteroaryl group;

$R^2$ represents a hydrogen atom or a $C_1$-$C_6$ alkyl group being unsubstituted or substituted with 1 to 2 substituents independently selected from the group consisting of a hydroxy group and a $C_1$-$C_6$ alkoxy group;

$R^3$ and $R^4$ independently represent a hydrogen atom, or a $C_1$-$C_6$ alkyl, $C_3$-$C_7$ cycloalkyl or heteroaryl group being unsubstituted or substituted with 1 to 3 substituents independently selected from the group consisting of a deuterium, a halogen atom, a hydroxy group, a $C_1$-$C_6$ alkoxy group and a $C_3$-$C_7$ cycloalkyl group; or $R^3$ and $R^4$ taken together with the nitrogen atom to which they are attached form a 4 to 6 membered heterocyclic group being unsubstituted or substituted with 1 to 2 substituents selected from the group consisting of a hydroxy group, an oxo group, a $C_1$-$C_6$ alkyl group, a $C_1$-$C_6$ acyl group, and a hydroxy-$C_1$-$C_6$ alkyl group;

A represents an aryl or heteroaryl group being unsubstituted or substituted with 1 to 5 substituents independently selected from the group consisting of a halogen atom, a $C_1$-$C_6$ alkyl group, a hydroxy-$C_1$-$C_6$ alkyl group, a $C_1$-$C_6$ alkoxy-substituted $C_1$-$C_6$ alkyl group, —$NR^5SO_2R^6$ and —$CONR^7R^8$;

$R^5$, $R^7$ and $R^8$ independently represent a hydrogen atom or a $C_1$-$C_6$ alkyl group;

$R^6$ represents a $C_1$-$C_6$ alkyl group; and

E represents an oxygen atom or NH.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, further comprising other pharmacologically active agent(s).

Also, the present invention provides a method for the treatment of a condition mediated by acid pump modulating activity in a mammalian subject including a human, which comprises administering to a mammal in need of such treatment a therapeutically effective amount of a compound of formula (I) or a pharmaceutically acceptable salt thereof, each as described herein.

Examples of conditions mediated by acid pump modulating activity include, but are not limited to, APA Diseases.

Further, the present invention provides the use of a compound of formula (I) or a pharmaceutically acceptable salt thereof, each as described herein, for the manufacture of a medicament for the treatment of a condition mediated by acid pump inhibitory activity.

Further, the present invention provides a compound of formula (I) or a pharmaceutically acceptable salt thereof, for use in medicine.

Preferably, the present invention also provides the use of a compound of formula (I) or a pharmaceutically acceptable salt thereof, each as described herein, for the manufacture of a medicament for the treatment of diseases selected from APA Diseases.

The compounds of the present invention may show good acid pump inhibitory activity, less toxicity, good absorption, good distribution, good solubility, less protein binding affinity other than acid pump, less drug-drug interaction and good metabolic stability.

DETAILED DESCRIPTION OF THE INVENTION

In the compounds of the present invention:

Where $R^2$, $R^3$, $R^4$, $R^5$, $R^6$, $R^7$, $R^8$, and the substituents of the 4 to 7 membered heterocyclic group and A are the $C_1$-$C_6$ alkyl group, this $C_1$-$C_6$ alkyl group may be a straight or branched chain group having one to six carbon atoms, and examples include, but are not limited to, methyl, ethyl, propyl, isopropyl, butyl, isobutyl, sec-butyl, tert-butyl, pentyl, 1-ethylpropyl and hexyl. Of these, $C_1$-$C_2$ alkyl is more preferred; methyl is more preferred.

Where $R^3$ and $R^4$ are the $C_3$-$C_7$ cycloalkyl group, this represents cycloalkyl group having three to seven carbon atoms, and examples include cyclopropyl, cyclobutyl, cyclopentyl, cyclohexyl and cycloheptyl. Of these, $C_3$-$C_5$ cycloalkyl group is preferred; cyclopropyl is more preferred.

Where the substituents of $R^1$, $R^3$ and $R^4$ are the $C_1$-$C_6$ alkoxy group, this represents the oxygen atom substituted with the said $C_1$-$C_6$ alkyl group, and examples include, but are not limited to, methoxy, ethoxy, propoxy, isopropoxy, butoxy, isobutoxy, sec-butoxy, tert-butoxy, pentyloxy and hexyloxy. Of these, a $C_1$-$C_4$ alkoxy is preferred; a $C_1$-$C_2$ alkoxy is preferred; methoxy is more preferred.

Where $R^3$ and $R^4$ taken together with the nitrogen atom to which they are attached form a 4 to 7 membered heterocyclic group, this 4 to 7 membered heterocyclic group represents a saturated heterocyclic group having three to six ring atoms selected from carbon atom, nitrogen atom, sulfur atom and oxygen atom other than said nitrogen atom, and examples include, but are not limited to, azetidinyl, pyrrolidinyl, imidazolidinyl, pyrazolidinyl, piperidyl, piperazinyl, hexahydroazepinyl, hexahydrodiazepinyl, morpholino, thiomorpholino and homomorpholino. Of these, azetidinyl, pyrrolidinyl, morpholino and homomorpholino are preferred; morpholino is more preferred.

Where the substituent of the 4 to 7 membered heterocyclic group or A is a hydroxy-$C_1$-$C_6$ alkyl group, this represents said $C_1$-$C_6$ alkyl group substituted with a hydroxy group, and examples include, but are not limited to, hydroxymethyl, 2-hydroxyethyl, 1-hydroxyethyl 3-hydroxypropyl, 2-hydroxypropyl, 2-hydroxy-1-methylethyl, 4-hydroxybutyl, 3-hydroxybutyl, 2-hydroxybutyl, 3-hydroxy-2-methylpropyl, 3-hydroxy-1-methylpropyl, 5-hydroxypentyl and 6-hydroxyhexyl. Of these, hydroxy-$C_1$-$C_3$ alkyl is preferred; hydroxymethyl is more preferred.

Where A and the substituents of $R^1$ are an aryl group, these may be phenyl, naphtyl or anthracenyl. Of these, phenyl is preferred.

Where the substituents of $R^3$, $R^4$ and A are a halogen atom, they may be a fluorine, chlorine, bromine or iodine atom. Of these, a fluorine atom and a chlorine atom are preferred.

Where the substituent of $R^1$ is a hydroxy-substituted aryl group, this hydroxy-substituted aryl group represents an aryl group which is substituted with hydroxy group(s) and the aryl group is aforementioned above. Examples include, but not limited to, 2-hydroxyphenyl, 3-hydroxyphenyl, 4-hydroxyphenyl, 2,3-dihydroxyphenyl, 2,4-dihydroxyphenyl, 3,5-dihydroxyphenyl, 1-hydroxynaphthyl, 2-hydroxynaphthyl, 1-hydroxyanthracenyl. Of these, 3-hydroxyphenyl is preferred.

Where A, $R^3$, $R^4$ or the substituents of $R^1$ are a heteroaryl group, this represents 5 to 6-membered ring containing at least one hetero atom selected from N, O and S, and examples include, but not limited to, 2-thienyl, 2-thiazolyl, 4-thiazolyl, 2-furyl, 2-oxazolyl, 1-pyrazolyl, 2-pyridyl, 3-pyridyl, 4-pyridyl, 2-pyrazinyl and 2-pyrimidinyl. Of these, the heteroaryl group containing at least one nitrogen atom is preferred; 2-thiazolyl, 4-thiazolyl and 1-pyrazolyl are more preferred for the substituent of $R^1$; 2-pyridyl, 3-pyridyl and 4-pyridyl are more preferred for A.

Where the substituent of $R^1$ is a hydroxy-substituted $C_3$-$C_7$ cycloalkyl group, this hydroxy-substituted $C_3$-$C_7$ cycloalkyl group represents a $C_3$-$C_7$ cycloalkyl group which is substituted with hydroxy group(s) and the $C_3$-$C_7$ cycloalkyl is aforementioned above. Examples of a hydroxy-substituted $C_3$-$C_7$ cycloalkyl group include, but are not limited to, 1-hydroxycyclopropyl, 2-hydroxycyclopropyl, 1-hydroxycyclobutyl, 2-hydroxycyclobutyl, 2,3-dihydroxycyclobutyl 2-hydroxycyclopentyl, 3-hydroxycyclopentyl, 1-hydroxycyclohexyl, 2-hydroxycyclohexyl, 3-hydroxycyclohexyl, 4-hydroxycyclohexyl, 2,4-dihydroxycyclohexyl, 3,5-dihydroxycyclohexyl, 1-hydroxycycloheptyl, 2-hydroxycycloheptyl, 3-hydroxycycloheptyl and 4-hydroxycycloheptyl. Of these, hydroxy-substituted $C_3$-$C_5$ cycloalkyl is preferred; 1-hydroxycyclopropyl is more preferred.

Where the substituent of $R^1$ is a hydroxy-$C_1$-$C_6$ alkyl-substituted $C_3$-$C_7$ cycloalkyl group, this hydroxy-$C_1$-$C_6$ alkyl-substituted $C_3$-$C_7$ cycloalkyl group represents a $C_3$-$C_7$ cycloalkyl group which is substituted with hydroxy-$C_1$-$C_6$ alkyl group(s), and the hydroxy-$C_1$-$C_6$ alkyl and the $C_3$-$C_7$ cycloalkyl are aforementioned above. Examples of a hydroxy-$C_1$-$C_6$ alkyl-substituted $C_3$-$C_7$ cycloalkyl group include, but are not limited to, 1-hydroxymethylcyclopropyl, 1-(2-hydroxyethyl)-cyclopropyl, 2-hydroxymethylcyclopropyl, 1-hydroxymethylcyclobutyl, 2-hydroxymethylcyclobutyl, 2,3-bis(hydroxymethyl)cyclobutyl, 1-hydroxymethylcyclopentyl, 2-hydroxymethylcyclopentyl, 3-hydroxymethylcyclopentyl, 1-hydroxymethylcyclohexyl, 2-hydroxymethylcyclohexyl, 3-hydroxymethylcyclohexyl, 4-hydroxymethylcyclohexyl, 1-hydroxymethylcycloheptyl, 2-hydroxymethylcycloheptyl, 3-hydroxymethylcycloheptyl and 4-hydroxymethylcycloheptyl. Of these, hydroxy-$C_1$-$C_3$ alkyl-substituted $C_3$-$C_5$ cycloalkyl is preferred; 1-hydroxymethylcyclopropyl and 1-(2-hydroxyethyl)-cyclopropyl are more preferred.

Where the substituent of $R^1$ is a halogen-substituted heteroaryl group, this halogen-substituted heteroaryl group represents a heteroaryl group which is substituted with halogen atom(s), and the halogen atom and the heteroaryl are aforementioned above. Examples of a halogen-substituted heteroaryl group include, but are not limited to, 4-fluoro-2-thienyl, 4-fluoro-2-thiazolyl, 2-fluoro-4-thiazolyl, 4-fluoro-2-furyl, 4-fluoro-2-oxazolyl, 4-fluoro-1-pyrazolyl, 4-fluoro-2-pyridyl, 5-fluoro-3-pyridyl, 3-fluoro-4-pyridyl, 3,4-difluoro-2-pyridyl, 3,5-difluoro-2-pyridyl, 5-fluoro-2- pyrazyl, 5-fluoro-2-pyrimidinyl, 4-chloro-2-thienyl, 4-chloro-2-thiazolyl, 2-chloro-4-thiazolyl, 4-chloro-2-furyl, 4-chloro-2-oxazolyl, 4-chloro-1-pyrazolyl, 4-chloro-2-pyridyl, 5-chloro-3-pyridyl, 3-chloro-4-pyridyl, 3,4-dichloro-2-pyridyl, 3,5-dichloro-2-pyridyl, 5-chloro-2-pyrazyl and 5-chloro-2-pyrimidinyl. Of these, 3,5-difluoro-2-pyridyl is preferred.

Where the substituent of A is a $C_1$-$C_6$ alkoxy-substituted $C_1$-$C_6$ alkyl group, this $C_1$-$C_6$ alkoxy-substituted $C_1$-$C_6$ alkyl group represents a $C_1$-$C_6$ alkyl group which is substituted by $C_1$-$C_6$ alkoxy group(s) and the $C_1$-$C_6$ alkoxy and the $C_1$-$C_6$ alkyl are aforementioned above. Examples of a $C_1$-$C_6$ alkoxy-substituted $C_1$-$C_6$ alkyl group include, but are not limited to, methoxymethyl, 2-methoxyethyl, 3-methoxypropyl, 4-methoxybutyl, 5-methoxypentyl, 6-methoxyhexyl, 1-ethoxymethyl, 2-ethoxyethyl, 3-ethoxypropyl, 4-ethoxybutyl, 5-ethoxypentyl. Of these, $C_1$-$C_3$ alkoxy-substituted $C_1$-$C_3$ alkyl is preferred; methoxymethyl is more preferred.

Where the substituents of the 4 to 6 membered heterocyclic group are a $C_1$-$C_6$ acyl group, this represents a carbonyl group substituted with hydrogen atom or the said $C_1$-$C_5$ alkyl group, and examples include, but are not limited to, a formyl, acetyl, propionyl, butyryl, pentanoyl and hexanoyl. Of these, $C_2$-$C_6$ acyl is preferred and acetyl is more preferred.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

Preferred classes of compounds of the present invention are those compounds of formula (I) or a pharmaceutically acceptable salt thereof, each as described herein, in which:
(a) $R^1$ is a $C_1$-$C_6$ alkyl group being substituted with 1 to 2 substituents independently selected from the group consisting of a hydroxy group, a $C_1$-$C_6$ alkoxy group, a hydroxy-substituted $C_3$-$C_7$ cycloalkyl group, a hydroxy-$C_1$-$C_6$ alkyl-substituted $C_3$-$C_7$ cycloalkyl group, an aryl group, a hydroxy-substituted aryl group, a heteroaryl group and a halogen-substituted heteroaryl group;
(b) $R^1$ is a $C_1$-$C_6$ alkyl group being substituted with 1 to 2 substituents independently selected from the group consisting of a hydroxy group, a $C_1$-$C_6$ alkoxy group or a heteroaryl group;
(c) $R^1$ is a $C_1$-$C_6$ alkyl group being substituted with a hydroxy group, $C_1$-$C_6$ alkoxy group or a heteroaryl group;
(d) $R^1$ is a $C_2$-$C_3$ alkyl group being substituted with a hydroxy group, a $C_1$-$C_3$ alkoxy group, an isoxazole group, a thiazolyl group or a pyrazolyl group;
(e) $R^1$ is a $C_2$-$C_3$ alkyl group being substituted with a hydroxy group, a methoxy group or an isoxazole group;
(f) $R^2$ is a $C_1$-$C_6$ alkyl group being unsubstituted or substituted with 1 to 2 substituents independently selected from the group consisting of a hydroxy group and a $C_1$-$C_6$ alkoxy group;
(g) $R^2$ is a $C_1$-$C_6$ alkyl group;
(h) $R^2$ is a $C_1$-$C_3$ alkyl group;
(i) $R^2$ is a methyl group;
(j) $R^3$ and $R^4$ are independently a hydrogen atom, or a $C_1$-$C_6$ alkyl, $C_3$-$C_7$ cycloalkyl or heteroaryl group being unsubstituted or substituted with 1 to 3 substituents independently selected from the group consisting of a deuterium, a halogen atom, a hydroxy group, a $C_1$-$C_6$ alkoxy group and a $C_3$-$C_7$ cycloalkyl group;
(k) $R^3$ and $R^4$ are independently a $C_1$-$C_6$ alkyl group being unsubstituted or substituted with one substituent selected from the group consisting of a hydroxy group and a $C_1$-$C_6$ alkoxy group or —$CD_3$;
(l) $R^3$ and $R^4$ are independently a hydrogen atom, a $C_1$-$C_3$ alkyl group being unsubstituted or substituted with a hydroxy group or —$CD_3$;
(m) $R^3$ and $R^4$ are independently a hydrogen atom, a methyl group, —$CD_3$ or 2-hydroxyethyl group;
(n) $R^3$ and $R^4$ are independently a methyl group, —$CD_3$ or 2-hydroxyethyl group;
(o) $R^3$ and $R^4$ taken together with the nitrogen atom to which they are attached form a 4 to 6 membered heterocyclic group being unsubstituted or substituted with 1 to 2 substituents selected from the group consisting of a hydroxy group, an oxo group, a $C_1$-$C_6$ alkyl group, a $C_1$-$C_6$ acyl group, and a hydroxy-$C_1$-$C_6$ alkyl group;
(p) $R^3$ and $R^4$ taken together with the nitrogen atom to which they are attached form an azetidinyl, pyrrolidinyl, piperazinyl or morpholino group being unsubstituted or substituted with 1 to 2 substituents selected from the group consisting of a hydroxy group, an oxo group, a $C_1$-$C_6$ alkyl group, a $C_1$-$C_6$ acyl group and a hydroxy-$C_1$-$C_6$ alkyl group;
(q) $R^3$ and $R^4$ taken together with the nitrogen atom to which they are attached form a piperazinyl or morpholino group being unsubstituted or substituted with 1 to 2 substituents selected from the group consisting of a hydroxy group, an oxo group and a hydroxy-$C_1$-$C_3$ alkyl group;
(r) $R^3$ and $R^4$ taken together with the nitrogen atom to which they are attached form a morpholino group;
(s) A is an aryl group being unsubstituted or substituted with 1 to 5 substituents independently selected from the group consisting of a halogen atom, a $C_1$-$C_6$ alkyl group, a hydroxy-$C_1$-$C_6$ alkyl group, a $C_1$-$C_6$ alkoxy-substituted $C_1$-$C_6$ alkyl group, —$NR^5SO_2R^6$ and —$CONR^7R^8$;
(t) A is an aryl group being unsubstituted or substituted with 1 to 5 substituents selected from the group consisting of hydrogen atom, a halogen atom, a $C_1$-$C_6$ alkyl group and a hydroxy-$C_1$-$C_6$ alkyl group;
(u) A is an aryl group being unsubstituted or substituted with 1 to 2 substituents selected from the group consisting of hydrogen atom, a fluorine atom, a methyl group and a hydroxymethyl group;
(v) A is an aryl group being unsubstituted or substituted with a halogen atom;
(w) A is a phenyl I group being unsubstituted or substituted with a fluorine atom;
(x) $R^5$ is a hydrogen atom or a $C_1$-$C_6$ alkyl group;
(y) $R^5$ is a hydrogen atom or a methyl group;
(z) $R^6$ is a $C_1$-$C_4$ alkyl group;
(aa) $R^6$ is a methyl group
(bb) $R^7$ is a hydrogen atom or a $C_1$-$C_6$ alkyl group;
(cc) $R^7$ is a hydrogen atom or a methyl group;
(dd) $R^8$ is a hydrogen atom or a $C_1$-$C_6$ alkyl group;
(ee) $R^8$ is a hydrogen atom or a methyl group;
(ff) E is an oxygen atom.

Of these classes of compounds, any combination among (a) to (ff) is also preferred.

Preferred compounds of the present invention are those compounds of formula (I) or a pharmaceutically acceptable salt thereof, each as described herein, in which:
(A) $R^1$ is a $C_1$-$C_6$ alkyl group being substituted with 1 to 2 substituents independently selected from the group consisting of a hydroxy group, a $C_1$-$C_6$ alkoxy group and a heteroaryl group; $R^2$ is a $C_1$-$C_6$ alkyl group; $R^3$ and $R^4$ are independently a hydrogen atom or a $C_1$-$C_6$ alkyl being unsubstituted or substituted with 1 to 3 substituents independently selected from the group consisting of a deuterium, a hydroxy group and a $C_1$-$C_6$ alkoxy group; or $R^3$ and $R^4$ taken together with the nitrogen atom to which they are attached form a 4 to 6 membered heterocyclic group being unsubstituted or substituted with 1 to 2 substituent selected from the group consisting of a hydroxy group, an oxo group, a $C_1$-$C_6$ alkyl group, a $C_1$-$C_6$ acyl group and a hydroxy-$C_1$-$C_6$ alkyl group; A is an aryl group being unsubstituted or substituted with 1 to 5 substituents independently selected from the group consisting of a halogen atom, a $C_1$-$C_6$ alkyl group, a hydroxy-$C_1$-$C_6$ alkyl group, a $C_1$-$C_6$ alkoxy-substituted $C_1$-$C_6$ alkyl group, —$NR^5SO_2R^6$ and —$CONR^7R^8$; $R^5$, $R^7$ and $R^8$ are independently a hydrogen atom or a $C_1$-$C_6$ alkyl group; and $R^6$ is a $C_1$-$C_6$ alkyl group; and E is an oxygen atom;

(B) $R^1$ is a $C_1$-$C_6$ alkyl group being substituted with 1 to 2 substituents independently selected from the group consisting of a hydroxy group, a $C_1$-$C_6$ alkoxy group or a heteroaryl group; $R^2$ is a $C_1$-$C_6$ alkyl group; $R^3$ and $R^4$ are independently a hydrogen atom, a $C_1$-$C_3$ alkyl group being unsubstituted or substituted with a hydroxy group or —$CD_3$; or $R^3$ and $R^4$ taken together with the nitrogen atom to which they are attached form an azetidinyl, pyrrolidinyl, piperazinyl or morpholino group being unsubstituted or substituted with 1 to 2 substituents selected from the group consisting of a hydroxy group, an oxo group, a $C_1$-$C_6$ alkyl group, a $C_1$-$C_6$ acyl group and a hydroxy-$C_1$-$C_6$ alkyl group; A is an aryl group being unsubstituted or substituted with 1 to 5 substituents independently selected from the group consisting of a halogen atom, a $C_1$-$C_6$ alkyl group, a hydroxy-$C_1$-$C_6$ alkyl group, a $C_1$-$C_6$ alkoxy-substituted $C_1$-$C_6$ alkyl group, —$NR^5SO_2R^6$ and —$CONR^7R^8$; $R^5$, $R^7$ and $R^8$ are independently a hydrogen atom or a $C_1$-$C_6$ alkyl group; and $R^6$ is a $C_1$-$C_6$ alkyl group; and E is an oxygen atom;

(C) $R^1$ is a $C_1$-$C_6$ alkyl group being substituted with 1 to 2 substituents independently selected from the group consisting of a hydroxy group, a $C_1$-$C_6$ alkoxy group or a heteroaryl group; $R^2$ is a $C_1$-$C_6$ alkyl group; $R^3$ and $R^4$ are independently a hydrogen atom, a $C_1$-$C_3$ alkyl group being unsubstituted or substituted with a hydroxy group or —$CD_3$; or $R^3$ and $R^4$ taken together with the nitrogen atom to which they are attached form an azetidinyl, pyrrolidinyl, piperazinyl or morpholino group being unsubstituted or substituted with 1 to 2 substituents selected from the group consisting of a hydroxy group, an oxo group, a $C_1$-$C_6$ alkyl group, a $C_1$-$C_6$ acyl group and a hydroxy-$C_1$-$C_6$ alkyl group; A is an aryl group being unsubstituted or substituted with 1 to 5 substituents selected from the group consisting of hydrogen atom, a halogen atom, a $C_1$-$C_6$ alkyl group and a hydroxy-$C_1$-$C_6$ alkyl group;

(D) $R^1$ is a $C_1$-$C_6$ alkyl group being substituted with 1 to 2 substituents independently selected from the group consisting of a hydroxy group, a $C_1$-$C_6$ alkoxy group or a heteroaryl group; $R^2$ is a methyl group; $R^3$ and $R^4$ are independently a hydrogen atom, a methyl group, —$CD_3$ or 2-hydroxyethyl group; or $R^3$ and $R^4$ taken together with the nitrogen atom to which they are attached form an azetidinyl, pyrrolidinyl, piperazinyl or morpholino group being unsubstituted or substituted with 1 to 2 substituents selected from the group consisting of a hydroxy group, an oxo group, a $C_1$-$C_6$ alkyl group, a $C_1$-$C_6$ acyl group and a hydroxy-$C_1$-$C_6$ alkyl group; A is an aryl group being unsubstituted or substituted with 1 to 5 substituents selected from the group consisting of hydrogen atom, a halogen atom, a $C_1$-$C_6$ alkyl group and a hydroxy-$C_1$-$C_6$ alkyl group;

(E) $R^1$ is a $C_1$-$C_6$ alkyl group being substituted with 1 to 2 substituents independently selected from the group consisting of a hydroxy group, a $C_1$-$C_6$ alkoxy group or a heteroaryl group; $R^2$ is a methyl group; $R^3$ and $R^4$ are independently a hydrogen atom, a methyl group, —$CD_3$ or 2-hydroxyethyl group; or $R^3$ and $R^4$ taken together with the nitrogen atom to which they are attached form a piperazinyl or morpholino group being unsubstituted or substituted with 1 to 2 substituents selected from the group consisting of a hydroxy group, an oxo group and a hydroxy-$C_1$-$C_3$ alkyl group; a $C_1$-$C_6$ alkyl group, a $C_1$-$C_6$ acyl group and a hydroxy-$C_1$-$C_6$ alkyl group; A is an aryl group being unsubstituted or substituted with 1 to 5 substituents selected from the group consisting of hydrogen atom, a halogen atom, a $C_1$-$C_6$ alkyl group and a hydroxy-$C_1$-$C_6$ alkyl group;

(F) $R^1$ is a $C_1$-$C_6$ alkyl group being substituted with a hydroxy group, a $C_1$-$C_6$ alkoxy group or a heteroaryl group; $R^2$ is a $C_1$-$C_6$ alkyl group; $R^3$ and $R^4$ are independently a hydrogen atom, a methyl group, —$CD_3$ or 2-hydroxyethyl group; or $R^3$ and $R^4$ taken together with the nitrogen atom to which they are attached form a morpholino group; A is an aryl group being unsubstituted or substituted with a halogen atom; and E is an oxygen atom.

The compounds of formula (I) containing one or more asymmetric carbon atoms can exist as two or more stereoisomers.

Included within the scope of the present invention are all stereoisomers and geometric isomers of the compounds of formula (I), including compounds exhibiting more than one type of isomerism, and mixtures of one or more thereof. Also included are acid addition salts wherein the counterion is optically active, for example, D-lactate or L-lysine, or racemate, DL-tartrate or DL-arginine.

One embodiment of the invention provides a compound selected from the group consisting of:

(−)-1-(2-methoxyethyl)-N,N,2-trimethyl-8-phenyl-1,6,7,8-tetrahydrochromeno[7,8-d]imidazole-5-carboxamide;

(−)-8-(4-fluorophenyl)-1-(2-methoxyethyl)-N,N,2-trimethyl-1,6,7,8-tetrahydrochromeno[7,8-d]imidazole-5-carboxamide 8-(4-fluorophenyl)-1-(3-hydroxypropyl)-N,N,2-trimethyl-1,6,7,8-tetrahydrochromeno[7,8-d]imidazole-5-carboxamide;

8-(4-fluorophenyl)-1-(isoxazol-3-ylmethyl)-N,N,2-trimethyl-1,6,7,8-tetrahydrochromeno[7,8-d]imidazole-5-carboxamide;

N,N-di[$^2H_3$]methyl-1-(2-methoxyethyl)-2-methyl-8-phenyl-1,6,7,8-tetrahydrochromeno[7,8-d]imidazole-5-carboxamide;

8-(4-fluorophenyl)-N-(2-hydroxyethyl)-1-(2-methoxyethyl)-N,2-dimethyl-1,6,7,8-tetrahydrochromeno[8,7-d]imidazole-5-carboxamide;

(8-(4-fluorophenyl)-1-(2-methoxyethyl)-2-methyl-1,6,7,8-tetrahydrochromeno[8,7-d]imidazol-5-yl)(morpholino)methanone or a pharmaceutically acceptable salt thereof.

Pharmaceutically acceptable salts of a compound of formula (I) include the acid addition salts (including disalts) thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

For a review on suitable salts, see "Handbook of Pharmaceutical Salts: Properties, Selection, and Use" by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

Pharmaceutically acceptable salts of the compounds of the invention include both unsolvated and solvated forms. The term "solvate" is used herein to describe a molecular complex comprising a compound of the invention and one or more pharmaceutically acceptable solvent molecules, for example, ethanol. The term 'hydrate' is employed when said solvent is water.

Pharmaceutically acceptable solvates in accordance with the invention include hydrates and solvates wherein the solvent of crystallization may be isotopically substituted, e.g. $D_2O$, $d_6$-acetone, $d_6$-DMSO.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see *J Pharm Sci*, 64 (8), 1269-1288 by Haleblian (August 1975).

The compounds of formula (I) may exist in one or more crystalline forms. These polymorphs, including mixtures thereof are also included within the scope of the present invention.

The compounds of formula (I) containing one or more asymmetric carbon atoms can exist as two or more stereoisomers.

Included within the scope of the present invention are all stereoisomers of the compounds of formula (I), including compounds exhibiting more than one type of isomerism, and mixtures of one or more thereof.

The present invention includes all pharmaceutically acceptable isotopically-labeled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labeled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labeled compounds of formula (I) can generally be prepared by conventional techniques known to those skilled in the art or by processes analogous to those described in the accompanying examples and preparations using an appropriate isotopically-labeled reagents in place of the non-labeled reagent previously employed.

All of the compounds of the formula (I) can be prepared by the procedures described in the general methods presented below or by the specific methods described in the examples section and the preparations section, or by routine modifications thereof. The present invention also encompasses any one or more of these processes for preparing the compounds of formula (I), in addition to any novel intermediates used therein.

General Synthesis

The compounds of the present invention may be prepared by a variety of processes well known for the preparation of compounds of this type, for example as shown in the following Method A and B.

Unless otherwise indicated, $R^1$, $R^2$, $R^3$, $R^4$, $R^5$, $R^6$, $R^7$, $R^8$, A and E in the following methods are as defined above. All starting materials in the following general syntheses may be commercially available or obtained by conventional methods known to those skilled in the art, such as WO 2004054984 and the disclosures of which are incorporated herein by references.

Method A

This illustrates the preparation of compounds of formula (Ia) wherein E is an oxygen atom.

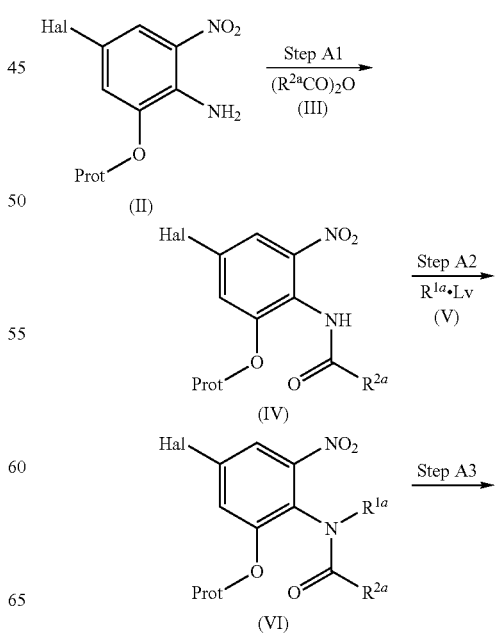

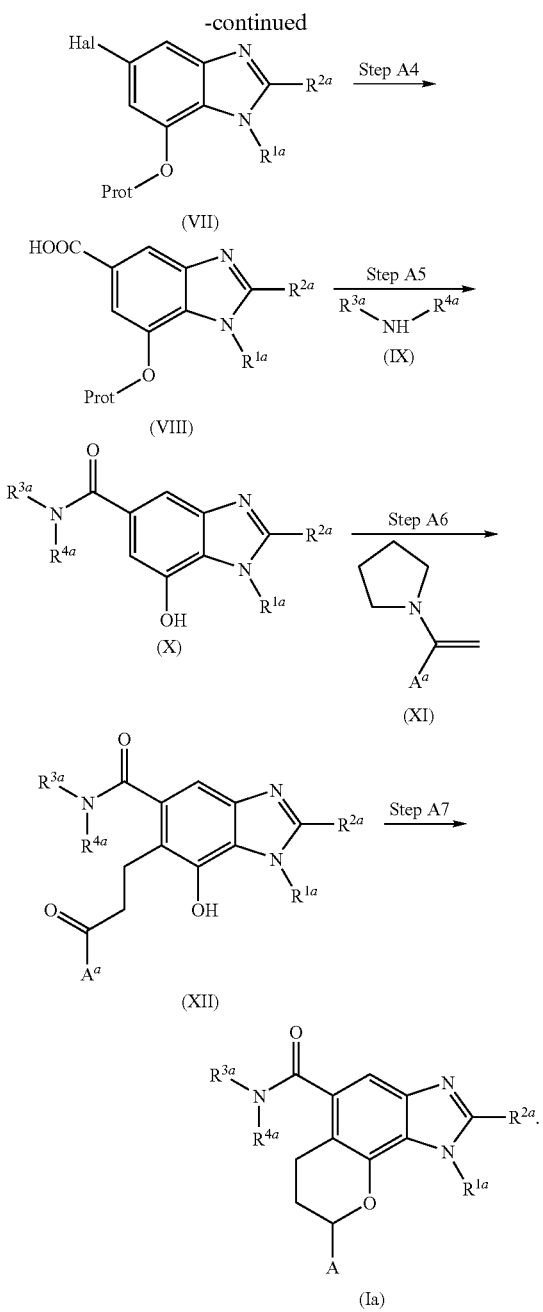

In Reaction Scheme A, $R^1$, $R^2$, $R^3$, $R^4$ and A are each as defined above; Hal is a halogen atom, preferably a bromine atom; Lv is a leaving group; $R^{1a}$ is $R^1$ as defined above or $R^1$ wherein hydroxy group is protected by a hydroxy-protecting group; $R^{2a}$ is $R^2$ as defined above or $R^2$ wherein hydroxy group is protected by a hydroxy-protecting group; $R^{3a}$ is $R^3$ as defined above or $R^3$ wherein hydroxy group is protected by a hydroxy-protecting group; $R^{4a}$ is $R^4$ as defined above or $R^4$ wherein hydroxy group is protected by a hydroxy-protecting group; $A^a$ is A as defined above or A wherein hydroxy group is protected by a hydroxy-protecting group, Prot is hydroxy-protecting group; and the same shall apply hereinafter. The term "leaving group", as used herein, signifies a group capable of being substituted by nucleophilic groups, such as a hydroxy group or amines and examples of such leaving groups include a halogen atom, a alkylsulfonyloxy group, a halogenoalkylsulfonyloxy group and a phenylsulfonyloxy group. Of these, a bromine atom, a chlorine atom, a methylsulfonyloxy group, a trifluoromethylsulfonyloxy group and a 4-methylphenylsulfonyloxy group are preferred.

The term "hydroxy-protecting groups", as used herein, signifies a protecting group capable of being cleaved by various means to yield a hydroxy group, such as hydrogenolysis, hydrolysis, electrolysis or photolysis, and such hydroxy-protecting groups are described in Protective Groups in Organic Synthesis edited by T. W. Greene et al. (John Wiley & Sons, 1999). Such as for example, $C_1$-$C_6$ alkoxycarbonyl, $C_1$-$C_6$ alkylcarbonyl, tri-$C_1$-$C_6$ alkylsilyl or tri-$C_1$-$C_8$ alkylarylsilyl groups, and $C_1$-$C_6$ alkoxy-$C_1$-$C_6$ alkyl groups. Suitable hydroxy-protecting groups include acetyl and tert-butyldimethylsilyl.

(Step A1)

In this step, the compound (IV) is prepared by amide formation of the amino group of the compound of formula (II), which is commercially available or may be prepared by the methods described in WO 2004054984, with acid anhydride (III).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; carboxylic acids, such as acetic acid; aromatic hydrocarbons, such as benzene, toluene and nitrobenzene; amides, such as formamide, N,N-dimethylformamide, N,N-dimethylacetamide and hexamethylphosphoric triamide; Of these solvents, acetic acid is preferred.

The reaction may be carried out in the presence of an acid. There is likewise no particular restriction on the nature of the acids used, and any acid commonly used in reactions of this type may equally be used here. Examples of such acids include: acids, such as hydrochloric acid, sulfuric acid or hydrobromic acid; sulfonic acids, such as methanesulfonic acid or toluenesulfonic acid. Of these, sulfuric acid is preferred.

The reaction may be carried out in the presence or absence of a base. There is likewise no particular restriction on the nature of the bases used, and any base commonly used in reactions of this type may equally be used here. Examples of such bases include: amines, such as N-methylmorpholine, triethylamine, tripropylamine, tributylamine, diisopropylethylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). Of these, the reaction in the absence of base is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

(Step A2)

In this step, the compound of formula (VI) is prepared by the nucleophilic substitution of the compound of formula (IV) with the compound of formula (V).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; nitriles, such as acetonitrile and benzonitrile; and sulfoxides, such as dimethyl sulfoxide and sulfolane. Of these solvents, N,N-dimethylformamide is preferred.

The reaction is carried out in the presence of a base. There is likewise no particular restriction on the nature of the bases used, and any base commonly used in reactions of this type may equally be used here. Examples of such bases include: alkali metal hydrides, such as lithium hydride, sodium hydride and potassium hydride; and alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, sodium hydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 80° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours, will usually suffice.

(Step A3)

In this step, the compound of formula (VII) is prepared by reduction and cyclization of the compound of formula (VI).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; carboxylic acids, such as acetic acid; amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; Of these solvents, acetic acid is preferred.

The reaction is carried out in the presence of a reducing agent. There is likewise no particular restriction on the nature of the reducing agents used, and any reducing agent commonly used in reactions of this type may equally be used here. Examples of such reducing agents include: a combination of metals, such as zinc and iron, and acids, such as hydrochloric acid, acetic acid and acetic acid-ammonium chloride complex; a combination of a hydrogen supplier, such as hydrogen gas and ammonium formate, and a catalyst, such as palladium-carbon, platinum and Raney nickel; Of these, the combination of iron and acetic acid or a combination of hydrogen gas and palladium carbon is preferred.

The reaction may be carried out in the presence of an acid. There is likewise no particular restriction on the nature of the acids used, and any acid commonly used in reactions of this type may equally be used here. Examples of such acids include: acids, such as hydrochloric acid, sulfuric acid or hydrobromic acid; carboxylic acids, such as acetic acid; sulfonic acids, such as methanesulfonic acid or toluenesulfonic acid. Of these, acetic acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours will usually suffice.

(Step A4)

In this step, the compound of formula (VIII) is prepared by substitution of the halogen atom of the compound of formula (VII) with metal cyanide (A4a) followed by hydrolysis (A4b).

(A4a) Substitution of Halogen Atom

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide, 1-methylpyrrolidin-2-one and hexamethylphosphoric triamide; Of these solvents, N,N-dimethylformamide is preferred.

The reaction is carried out in the presence of a metal cyanide reagent. There is no particular restriction on the nature of the metal cyanide reagent to be employed, and any metal cyanide reagent commonly used in reactions of this type may equally be used here. Examples of such metal cyanide reagents include: zinc(II) cyanide, copper(I) cyanide, potassium cyanide and sodium cyanide; Of these, zinc(II) cyanide is preferred.

The reaction is carried out in the presence or absence of a palladium catalyst. There is no particular restriction on the nature of the palladium catalyst to be employed, and any palladium catalyst commonly used in reactions of this type may equally be used here. Examples of such palladium catalysts include: a palladium metal, palladium chloride, palladium (II) acetate, tris(dibenzylideneacetone)dipalladium-chloroform, allyl palladium chloride, [1,2-bis(diphenylphosphino)ethane]palladium dichloride, bis(tri-o-tolylphosphine)palladium dichloride, bis(triphenylphosphine)palladium dichloride, tetrakis(triphenylphosphine)palladium, dichloro[1,1'-bis(diphenylphosphino)ferrocene]palladium, or a catalyst produced in solution by adding a ligand into the reaction solution of these. The ligand added into the reaction solution may be a phosphoric ligand such as triphenylphosphine, 1,1'-bis(diphenylphosphino)ferrocene, bis(2-diphenylphosphinophenyl)ether, 2,2'-bis(diphenylphosphino)-1,1'-binaphthol, 1,3-bis(diphenylphosphino)propane, 1,4-bis (diphenylphosphino)butane, tri-o-tolylphosphine, 2-diphenylphosphino-2'-methoxy-1,1'-binaphthyl or 2,2-bis (diphenylphosphino)-1,1'-binaphthyl. Of these, tetrakis (triphenylphosphine)palladium is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 50° C. to about 150° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours will usually suffice.

In this reaction, microwave can be employed to accelerate the reaction. In the case of employing microwave in sealed tube, the reaction at a temperature may be from about 50° C. to about 180° C. and the reaction time from about 5 minutes to about 12 hours will usually suffice.

(A4b) Hydrolysis

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; alcohols, such as methanol, ethanol, propanol, 2-propanol, butanol and ethylene glycol; sulfoxides, such as dimethyl sulfoxide and sulfolane; water; or mixed solvents thereof. Of these solvents, methanol, ethanol, tetrahydrofuran or ethylene glycol is preferred.

The reaction may be carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal carbonates, such as lithium carbonate, sodium carbonate and potassium carbonate. Of these, potassium hydroxide, lithium hydroxide or sodium hydroxide is preferred.

The reaction may be carried out in the presence of an acid. There is likewise no particular restriction on the nature of the acids used, and any acid commonly used in reactions of this type may equally be used here. Examples of such acids include: carboxylic acids, such as acetic acid or propionic acid; acids, such as hydrochloric acid, sulfuric acid or hydrobromic acid. Of these, hydrochloric acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 150° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 24 hours, will usually, suffice.

In this reaction, microwave can be employed to accelerate the reaction. In the case of employing microwave in sealed tube, the reaction at a temperature may be from about 50° C. to about 180° C. and the reaction time from about 5 minutes to about 12 hours will usually suffice.

(Step A5)

In this step, the compound (X) is prepared by amidation of the compound of formula (VIII) with the compound of formula (IX), which is commercially available or described in J. Org. Chem., 5935 (1990) and Canadian Journal of Chemistry, 2028 (1993).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; aromatic hydrocarbons, such as benzene, toluene and nitrobenzene; amides, such as formamide, N,N-dimethylformamide, N,N-dimethylacetamide and hexamethylphosphoric triamide; nitriles, such as acetonitrile and benzonitrile; sulfoxides, such as dimethyl sulfoxide and sulfolane; or mixed solvents thereof. Of these, N,N-dimethylformamide is preferred.

The reaction is carried out in the presence of a base. There is likewise no particular restriction on the nature of the bases used, and any base commonly used in reactions of this type may equally be used here. Examples of such bases include: amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di (tert-butyl)-4-methylpyridine, quinoline, N,N-dimethylaniline, N,N-diethylaniline, DBN, DABCO, and DBU. Of these, triethylamine or diisopropylethylamine is preferred.

The reaction is carried out in the presence of a condensing agent. There is likewise no particular restriction on the nature of the condensing agents used, and any condensing agent commonly used in reactions of this type may equally be used here. Examples of such condensing agents include: 2-halo-1-lower alkyl pyridinium salts, such as 2-chloro-1-methylpyridinium iodide and 2-bromo-1-ethylpyridinium tetrafluoroborate (BEP); diarylphosphoryl azides, such as diphenylphosphoryl azide (DPPA); chloroformates, such as ethyl chloroformate and isobutyl chloroformate; phosphorocyanidates, such as diethyl phosphorocyanidate (DEPC); imidazole derivatives, such as N,N'-carbonyldiimidazole (CDI); carbodiimide derivatives, such as N,N'-dicyclohexylcarbodiimide (DCC) and 1-(3-dimethylaminopropyl)-3-ethylcarbodiimide hydrochloride (EDCI); iminium salts, such as 2-(1H-benzotriazol-1-yl)-1,1,3,3-tetramethyluronium hexafluorophosphate (HBTU) and tetramethyl fluoroformamidinium hexafluorophosphate (TFFH); and phosphonium salts, such as benzotriazol-1-yloxytris(dimethylamino)phosphonium hexafluorophosphate (BOP) and bromo-tris-pyrrolidino-phosphonium hexafluorophosphate (PyBrop). Of these, EDCI or HBTU is preferred.

Reagents, such as 4-(N,N-dimethylamino)pyridine (DMAP), and 1-hydroxybenztriazole (HOBt), may be employed for this step. Of these, HOBt is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 80° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 48 hours, will usually suffice.

Following this reaction, Prot[1] may be deprotected as follows.

(Deprotection of Prot)

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; alcohols, such as methanol, ethanol, propanol, 2-propanol and butanol; carboxylic acid, such as acetic acid or formic acid; Of these solvents, methanol is preferred.

The reaction is carried out in the presence of a palladium catalyst under the hydrogen gas. There is no particular restriction on the nature of the palladium catalyst to be employed, and any palladium catalyst commonly used in reactions of this type may equally be used here. Examples of such palladium catalysts include: palladium metal, palladium-carbon, palladium hydroxide, Of these, palladium-carbon or palladium hydroxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

(Step A6)

In this step, the compound (XII) is prepared by Mannich reaction of the compound of formula (X) with Eshenmoser's salt (N,N-dimethylmethyleneiminium iodide) (A6a), followed by the coupling reaction with the compound of formula (XI)(A6b). The compound of formula (XI) is commercially available or may be prepared by the methods described in *J. Am. Chem. Soc.*, 1994, 116, 5985-5986.

(A6a) Mannich Reaction

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; nitrites, such as acetonitrile; sulfoxides, such as dimethyl sulfoxide and sulfolane. Of these solvents, N,N-dimethylformamide or dichloromethane is preferred.

The reaction is carried out in the presence or absence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal carbonates, such as lithium carbonate, sodium carbonate and potassium carbonate; alkali metal hydrogencarbonates, such as lithium hydrogencarbonate, sodium hydrogencarbonate and potassium hydrogencarbonate. Of these, potassium carbonate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 100° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

(A6b) The Coupling Reaction with the Compound of Formula (XI)

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: aromatic hydrocarbons, such as benzene, toluene and nitrobenzene; amides, such as formamide, N,N-dimethylformamide, N,N-dimethylacetamide and hexamethylphosphoric triamide; nitriles, such as acetonitrile and benzonitrile; sulfoxides, such as dimethyl sulfoxide and sulfolane; ketones, such as acetone and diethylketone. Of these solvents, toluene is preferred.

The reaction can take place over a wide range of temperatures, and the precise reaction temperature is not critical, to the invention. The preferred reaction temperature will depend upon such factors as the nature of the solvent, and the starting materials. However, in general, it is convenient to carry out the reaction at a temperature of from about 0° C. to about 150° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

(Step A7)

In this step, the compound (Ia) is prepared by reduction of the compound of formula (XII) (A7a), followed by the ring formation reaction (A7b).

(A7a) Reduction

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; sulfoxides, such as dimethyl sulfoxide and sulfolane; alcohols, such as methanol, ethanol, propanol, 2-propanol and butanol; or mixed solvents thereof. Of these, methanol or tetrahydrofuran is preferred.

The reaction is carried out in the presence of a reducing agent. There is likewise no particular restriction on the nature of the reducing agents used, and any reducing agent commonly used in reactions of this type may equally be used here. Examples of such reducing agents include: metal borohydrides, such as sodium borohydride, lithium borohydride and sodium cyanoborohydride; hydride compounds, such as lithium aluminum hydride and diisobutyl aluminum hydride; and borane reagents, such as boran-tetrahydrofuran complex, boran-dimethyl sulfide complex (BMS) and 9-borabicyclo [3.3.1]nonane (9-BBN). Of these, sodium borohydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 80° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 8 hours will usually suffice.

(A7b) Ring Formation Reaction

The reaction may be effected in the presence of solvent. There is no particular restriction on the nature of the solvent to be employed, provided that it has no adverse effect on the reaction or the reagents involved and that it can dissolve reagents, at least to some extent. Examples of suitable solvents: include: aliphatic hydrocarbons, such as hexane, heptane and petroleum ether; halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; nitrites, such as acetonitrile and benzonitrile. Of these, tetrahydrofuran or toluene is preferred.

The reaction may be carried out in the presence of a condensing agent. There is likewise no particular restriction on the nature of the condensing agents used, and any condensing agent commonly used in reactions of this type may equally be used here. Examples of such condensing agents include: azodicarboxylic acid di-lower alkyl esters, such as diethyl azodicarboxylate (DEAD), diisopropyl azodicarboxylate (DIAD) and di-tert-butyl azodicarboxylate (DTAD); azodicarboxamides, such as N,N,N',N'-tetraisopropylazodicarboxamide (TIPA), 1,1'-(azodicarbonyl)dipiperidine (ADDP) and N,N,N',N'-tetramethylazodicarboxamide (TMAD); phosphoranes, such as (cyanomethylene)tributylphosphorane (CMBP) and (cyanomethylene)trimethylphosphorane (CMMP). Of these, DIAD or ADDP is preferred.

Phosphine reagents, such as triphenylphosphine, trimethylphosphine and tributylphosphine, may be employed for this step. Of these, triphenylphosphine or tributylphosphine is preferred.

Alternatively, the inorganic acids, such as sulphonic acid and phosphoric acid, and water may be used as solvent and condensing reagent. Of these, phosphoric acid water solution is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

Introduction of the Hydroxy-Protecting Group

In the case where $R^1$, $R^2$, $R^3$, $R^4$ or A has a hydroxy group, if necessary, the reaction may be accomplished by protecting the hydroxy group.

The introduction of the hydroxy-protecting group can be carried out at an appropriate step before the reaction affected by the hydroxy group.

This reaction is described in detail by T. W. Greene et al., Protective Groups in Organic Synthesis, 369-453, (1999), the disclosures of which are incorporated herein by reference. The following exemplifies a typical reaction involving the protecting group tert-butyldimethylsilyl.

For example, when the hydroxy-protecting group is a "tert-butyldimethylsilyl", this step is conducted by reacting with a desired hydroxy-protecting group halide in an inert solvent in the presence of a base.

Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; or mixed solvents thereof. Of these, tetrahydrofuran or N,N-dimethylformamide is preferred.

Examples of the hydroxy-protecting group halide usable in the above reaction include trimethylsilyl chloride, triethylsilyl chloride, tert-butyldimethylsilyl chloride, acetyl chloride are preferred.

Examples of the base include alkali metal hydroxides such as lithium hydroxide, sodium hydroxide and potassium hydroxide, alkali metal carbonates such as lithium carbonate, sodium carbonate and potassium carbonate, and organic amines such as triethylamine, tributylamine, N-methylmorpholine, pyridine, imidazole, 4-dimethylaminopyridine, picoline, lutidine, collidine, DBN and DBU. Out of these, triethylamine, imidazole, or pyridine is preferred. Upon use of an organic amine in the liquid form, it also serves as a solvent when used in large excess.

The protection reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

Deprotecting Step

In the case where $R^{1a}$, $R^{2a}$, $R^{3a}$, $R^{4a}$ or Aa has a protected hydroxy group, the deprotection reaction will follow to yield a hydroxy group. This reaction is described in detail by T. W. Greene et al., Protective Groups in Organic Synthesis, 369-453, (1999), the disclosures of which are incorporated herein by reference. The following exemplifies a typical reaction involving the protecting group tert-butyldimethylsilyl.

The deprotection of the hydroxyl groups is carried out with an acid, such as acetic acid, hydrogen fluoride, hydrogen fluoride-pyridine complex, or fluoride ion, such as tetrabutylammonium fluoride (TBAF).

The deprotection reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: alcohol, such as methanol, ethanol or mixed solvents thereof.

The deprotection reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C.: The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

Method B

This illustrates the preparation of compounds of formula (Ia) wherein E is NH.

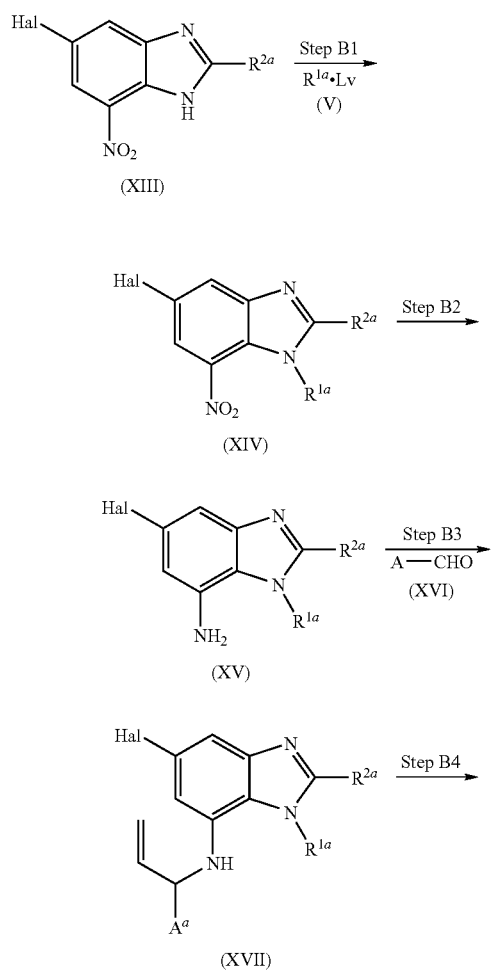

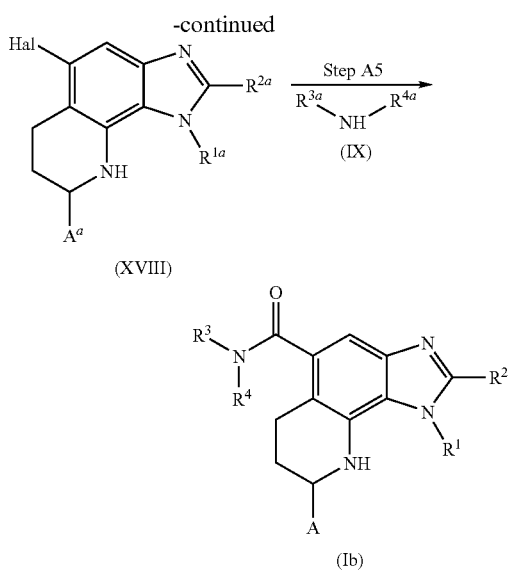

(Step B1)

In this step, the compound (XIV) is prepared by nucleophilic substitution of the compound of formula (XIII), which is commercially available or may be prepared by the methods described in WO2004087701, with the compound of formula (V). The reaction may be carried out under the same condition as described in Step A2 of Method A.

(Step B2)

In this step, the compound (XV) is prepared is prepared by reduction the compound of formula (XIV). The reaction may be carried out under the same condition as described in Step A3 of Method A.

(Step B3)

In this step, the compound (XVII) is prepared by imine formation of the compound of formula (XV) with the compound of formula (XVI) (B3a) followed by the reaction with vinylmagnesium bromide (B3b).

(B3a) Imine Formation

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; nitriles, such as acetonitrile and benzonitrile; sulfoxides, such as dimethyl sulfoxide and sulfolane; or mixed solvents thereof. Of these, toluene is preferred.

The reaction may be carried out in the presence of an acid. There is likewise no particular restriction on the nature of the acids used, and any acid commonly used in reactions of this type may equally be used here. Examples of such acids include: acids, such as hydrochloric acid, sulfuric acid or hydrobromic acid; sulfonic acids, such as methanesulfonic acid or toluenesulfonic acid; carboxylic acids, such as acetic acid. Of these, toluenesulfonic acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

(B3b) Reaction with Vinylmagnesium Bromide

The reaction may be effected in the presence of solvent. There is no particular restriction on the nature of the solvent to be employed, provided that it has no adverse effect on the reaction or the reagents involved and that it can dissolve reagents, at least to some extent. Examples of suitable solvents include: aliphatic hydrocarbons, such as hexane, heptane and petroleum ether; ethers, such as diethyl ether, diisopropyl ether, tetrahydrofuran and dioxane; aromatic hydrocarbons, such as benzene and toluene. Of these, tetrahydrofuran is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 100° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

(Step B4)

In this step, the compound (XVIII) is prepared by amino-Claisen rearrangement of the compound of formula (XVII) by heat (B4a), followed by the cyclization (B4b).

(B4a) Amino-Claisen Rearrangement

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; aromatic hydrocarbons, such as benzene, toluene and xylene; or mixed solvents thereof. Of these, toluene is preferred.

The reaction may be carried out in the presence of an acid. There is likewise no particular restriction on the nature of the acids used, and any acid commonly used in reactions of this type may equally be used here. Examples of such acids include: acids, such as hydrochloric acid, sulfuric acid or hydrobromic acid; sulfonic acids, such as methanesulfonic acid or toluenesulfonic acid; Lewis acid, such as boron trifluoride-diethyl etherate or zinc chloride. Of these, toluenesulfonic acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 150° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 48 hours, will usually suffice.

(B4b) Cyclization

The reaction is normally and preferably effected in the presence the inorganic acids, such as sulphonic acid and phosphoric acid, and water. Both may be used as solvent and condensing reagent. Of these, phosphoric acid water solution is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

(Step B5)

In this step, the compound of formula (Ib) is prepared by the conversion of the halogen atom into carboxyl group within the compound of formula (XVIII) followed by the amidation with the compound of formula (IX). The reaction may be carried out under the same condition as described in Step A4 and A5 of Method A.

The preparation/isolation of individual enantiomers can be prepared by conventional techniques, such as chiral synthesis from a suitable optically pure precursor or resolution of the racemate (or the racemate of a salt or derivative) using, for example, chiral high-pressure liquid chromatography (HPLC) and supercritical fluid chromatography (SFC).

Alternatively, a method of optical resolution of a racemate (or a racemic precursor) can be appropriately selected from conventional procedures, for example, preferential crystallization, or resolution of diastereomeric salts between a basic moiety of the compound of formula (I) and a suitable optically active acid such as tartaric acid.

The compounds of formula (I), and the intermediates in the above-mentioned preparation methods can be isolated and purified by conventional procedures, such as distillation, recrystallization or chromatographic purification.

Compounds of the invention intended for pharmaceutical use may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a pharmaceutical composition or formulation in association with one or more pharmaceutically acceptable carriers or excipients. The term "carrier" or "excipient" is used herein to describe any ingredient other than the compound(s) of the invention. The choice of carrier or excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in *Expert Opinion in Therapeutic Patents*, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface-active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "*Pharmaceutical Dosage Forms: Tablets, Vol. 1*", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, *Pharmaceutical Technology On-line*, 25(2), 1-14 (2001). The use of chewing gum to achieve controlled release is described in WO00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from about 3 to about 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, *J Pharm Sci*, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from about 1 µg to about 20 mg of the compound of the invention per actuation and the actuation volume may vary from about 1 µl to about 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from about 1 to about 100 µg of the compound of formula (I). The overall daily dose will typically be in the range about 50 µg to about 20 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in. WO91/11172, WO94/02518 and WO98/55148.

Kit-Of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range of about 0.05 mg to about 500 mg depending, of course, on the mode of administration, preferred in the range of about 0.1 mg to about 400 mg and more preferred in the range of about 0.5 mg to about 300 mg. For example, oral administration may require a total daily dose of from about 1 mg to about 300 mg, while an intravenous dose may only require from about 0.5 mg to about 100 mg. The total daily dose may be administered in single or divided doses.

These dosages are based on an average human subject having a weight of about 65 kg to about 70 kg. The physician will readily be able to determine doses for subjects whose weight falls outside this range, such as infants and the elderly.

Combinations

As discussed above, a compound of the invention exhibits acid pump inhibitory activity. An acid pump antagonist of the present invention may be usefully combined with another pharmacologically active compound, or with two or more other pharmacologically active compounds, particularly in the treatment of gastroesophageal reflux disease. For example, an acid pump antagonist, particularly a compound of the formula (I), or a pharmaceutically acceptable salt thereof, as defined above, may be administered simultaneously, sequentially or separately in combination with one or more agents selected from:

(i) histamine $H_2$ receptor antagonists, e.g. ranitidine, lafutidine, nizatidine, cimetidine, famotidine and roxatidine;

(ii) proton pump inhibitors, e.g. omeprazole, esomeprazole, pantoprazole, rabeprazole, tenatoprazole, ilaprazole and lansoprazole;

(iii) oral antacid mixtures, e.g. Maalox®, Aludrox® and Gaviscon®;

(iv) mucosal protective agents, e.g. polaprezinc, ecabet sodium, rebamipide, teprenone, cetraxate, sucralfate, chloropylline-copper and plaunotol;

(v) anti-gastric agents, e.g. Anti-gastrin vaccine, itriglumide and Z-360;

(vi) 5-$HT_3$ antagonists, e.g. dolasetron, palonosetron, alosetron, azasetron, ramosetron, mitrazapine, granisetron, tropisetron, E-3620, ondansetron and indisetron;

(vii) 5-$HT_4$ agonists, e.g. tegaserod, mosapride, cinitapride and oxtriptane;

(viii) laxatives, e.g. Trifyba®, Fybogel®, Konsyl®, Isogel®, Regulan®, Celevac® and Normacol®;

(ix) $GABA_B$ agonists, e.g. baclofen and AZD-3355;

(x) $GABA_B$ antagonists, e.g. GAS-360 and SGS-742;

(xi) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xii) dopamine antagonists, e.g. metoclopramide, domperidone and levosulpiride;

(xiii) Tachykinin (NK) antagonists, particularly NK-3, NK-2 and NK-1 antagonists, e.g. nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S);

(xiv) *Helicobacter pylori* infection agents, e.g. clarithromycin, roxithromycin, rokitamycin, flurithromycin, telithromycin, amoxicillin, ampicillin, temocillin, bacampicillin, aspoxicillin, sultamicillin, piperacillin, lenampicillin, tetracycline, metronidazole, bithmuth citrate and bithmuth subsalicylate;

(xv) nitric oxide synthase inhibitors, e.g. GW-274150, tilarginine, P54, guanidioethyldisulfide and nitroflurbiprofen;

(xvi) vanilloid receptor 1 antagonists, e.g. AMG-517 and GW-705498;

(xvii) muscarinic receptor antagonists, e.g. trospium, solifenacin, tolterodine, tiotropium, cimetropium, oxitropium, ipratropium, tiquizium, dalifenacin and imidafenacin;

(xviii) calmodulin antagonists, e.g. squalamine and DY-9760;

(xix) potassium channel agonists, e.g. pinacidil, tilisolol, nicorandil, NS-8 and retigabine;

(xx) beta-1 agonists, e.g. dobutamine, denopamine, xamoterol, denopamine, docarpamine and xamoterol;

(xxi) beta-2 agonists, e.g. salbutamol; terbutaline, arformoterol, meluadrine, mabuterol, ritodrine, fenoterol, clenbuterol, formoterol, procaterol, tulobuterol, pirbuterol, bambuterol, tulobuterol, dopexamine and levosalbutamol;

(xxii) beta agonists, e.g. isoproterenol and terbutaline;

(xxiii) alpha 2 agonists, e.g. clonidine, medetomidine, lofexidine, moxonidine, tizanidine, guanfacine, guanabenz, talipexole and dexmedetomidine;

(xxiv) endthelin A antagonists, e.g. bonsetan, atrasentan, ambrisentan, clazosentan, sitaxsentan, fandosentan and darusentan;

(xxv) opioid μ agonists, e.g. morphine, fentanyl and loperamide;

(xxvi) opioid μ antagonists, e.g. naloxone, buprenorphine and alvimopan;

(xxvii) motilin agonists, e.g. erythromycin, mitemcinal, SLV-305 and atilmotin;

(xxviii) ghrelin agonists, e.g. capromorelin and TZP-101;

(xxix) AchE release stimulants, e.g. Z-338 and KW-5092;

(xxx) CCK-B antagonists, e.g. itriglumide, YF-476 and S-0509;

(xxxi) glucagon antagonists, e.g. N,N-2501 and A-770077;

(xxxii) piperacillin, lenampicillin, tetracycline, metronidazole, bithmuth citrate and bithmuth subsalicylate;

(xxxiii) Glucagon-like peptide-1 (GLP-1) antagonists, e.g. PNU-126814;

(xxxiv) small conductance calcium-activated potassium channel 3 (SK-3) antagonists, e.g. apamin, dequalinium, atracurium, pancuronium and tubocurarine.

(xxxv) mGluR5 antagonists, e.g. ADX-10059 and AFQ-056;

(xxxvi) 5-HT3 agonists, e.g. pumosetrag (DDP733);

(xxxvii) mGluR8 agonists, e.g. (S)-3,4-DCPG and mGluR8-A.

Method for Assessing Biological Activities:

The acid pump inhibitory activity and other biological activities of the compounds of this invention were determined by the following procedures. Symbols have their usual meanings: mL (milliliter(s)), μL (microliter(s)), Kg (kirogram(s)), g (gram(s)), mg (milligram(s)), μg (microgram(s)), pmol (pico molar(s)), mmol (milli molar(s)), M (molar mass (m$^3$/mol)), mM (milli molar mass), μM (micro molar mass), quant. (quantitative yield), nm (nanometer(s)), min (minute(s)), Cat# (catalog number), mV (millivolt(s)), ms (millisecond(s)), i.p. (intraperitoneal).

Preparation of Gastric Vesicles from Fresh Porcine Stomachs

The porcine gastric vesicles for Porcine gastric $H^+/K^+$-ATPase inhibition assays were prepared from mucous membrane in fresh porcine stomachs by homogenization with a tight-fitted polytetrafluoroethylene (Teflone®) homogenizer in 0.25 M sucrose at 4° C. The crude pellet was removed with centrifugation at 20,000 g for 30 min. Then supernatant was centrifuged at 100,000 g for 30 min. The resulting pellet was re-suspended in 0.25 M sucrose, and then subjected to density gradient centrifugation at 132,000 g for 90 min. The gastric vesicles were collected from interface on 0.25 M sucrose layer containing 7% Ficoll™ PM400 (Amersham Biosciences). This procedure was performed in a cold room.

Ion-leaky Porcine Gastric $H^+/K^+$-ATPase Inhibition

Ion-leaky porcine gastric $H^+/K^+$-ATPase inhibition was measured according to the modified method described in *Biochemical Pharmacology*, 1988, 37, 2231-2236.

The isolated vesicles were lyophilized, and then kept in deep-freezer until use. For enzyme assay, lyophilized vesicles were reconstituted with 3 mM MgSO$_4$ containing 40 mM Bis-tris (pH 6.4 at 37° C.).

Enzyme reaction was performed incubating 5 mM KCl, 3 mM Na$_2$ATP, 3 mM MgSO$_4$ and 1.0 µg of reconstituted vesicles for 30 minutes at 37° C. in a final 60 µl of reaction mixture (40 mM Bis-tris, pH 6.4) with or without the test compound. Enzyme reaction was stopped by adding 10% sodium dodecyl sulphate (SDS). Released inorganic phosphate from ATP was detected by incubation with mixture of 1 part of 35 mM ammonium molybdate tetrahydrate in 15 mM Zinc acetate hydrate and 4 parts of 10% ascorbic acid (pH 5.0), resulting in phosphomolybdate, which has optical density at 750 nm. All example compounds showed potent inhibitory activity.

The results of IC$_{50}$ values of the inhibitory activity for the compounds of following examples are shown in Table 1.

TABLE 1

| Example No. | IC$_{50}$ (µM) |
| --- | --- |
| 1 | 0.098 |
| 2 | 0.52 |
| 3 | 0.068 |
| 4 | 0.19 |
| 5 | 0.088 |
| 6 | 0.23 |
| 7 | 0.038 |
| 8 | 0.34 |
| 9 | 0.35 |
| 10 | 0.10 |
| 11 | 0.21 |
| 12 | 0.090 |
| 13 | 0.34 |
| 14 | 0.27 |
| 15 | 0.20 |
| 16 | 0.074 |
| 17 | 1.0 |

All the tested compounds showed acid pump antagonistic activity.

Ion-Tight Porcine Gastric H$^+$/K$^+$-ATPase Inhibition

Ion-tight porcine gastric H$^+$/K$^+$-ATPase inhibition was measured according to the modified method described in *Biochemical Pharmacology*, 1988, 37, 2231-2236.

The isolated vesicles were kept in deep-freezer until use. For enzyme assay, vesicles were diluted with 3 mM MgSO$_4$ containing 5 mM Tris (pH 7.4 at 37° C.).

Enzyme reaction was performed incubating 150 mM KCl, 3 mM Na$_2$ATP, 3 mM MgSO$_4$, 15 µM valinomycin and 3.0 µg of vesicles for 30 minutes at 37° C. in a final 60 µl of reaction mixture (5 mM Tris, pH 7.4) with or without the test compound. Enzyme reaction was stopped by adding 10% SDS. Released inorganic phosphate from ATP was detected by incubating with mixture of 1 part of 35 mM ammonium molybdate tetrahydrate in 15 mM Zinc acetate hydrate and 4 parts of 10% ascorbic acid (pH 5.0), resulting in phosphomolybdate, which has optical density at 750 nm.

Canine Kidney Na$^+$/K$^+$-ATPase Inhibition

The powdered canine kidney Na$^+$/K$^+$-ATPase (Sigma) was reconstituted with 3 mM MgSO$_4$ containing 40 mM Tris (pH 7.4 at 37° C.). Enzyme reaction was performed incubating 100 mM NaCl, 2 mM KCl, 3 mM Na$_2$ATP, 3 mM MgSO$_4$ and 12 µg of enzyme for 30 minutes at 37° C. in a final 60 µl of reaction mixture (40 mM Tris, pH 7.4) with or without the test compound. Enzyme reaction was stopped by adding 10% SDS. Released inorganic phosphate from ATP was detected by incubating with mixture of 1 part of 35 mM ammonium molybdate tetrahydrate in 15 mM Zinc acetate hydrate and 4 parts of 10% ascorbic acid (pH 5.0), resulting in phosphomolybdate, which has optical density at 750 nm.

Inhibition of Acid Secretion in the Gastric Lumen-Perfused Rat

Acid secretion in the gastric lumen-perfused rat was measured according to Watanabe et al. [Watanabe K et al., *J. Physiol.* (Paris) 2000; 94: 111-116].

Male Sprague-Dawley rats, 8 weeks old, deprived of food for 18 hours before the experiment with free access to water, were anesthetized with urethane (1.4 g/kg, i.p.) and tracheotomized. After a middle abdominal incision, a dual polyethylene cannula was inserted into the forestomach and the stomach was perfused with saline (37° C., pH 5.0) at a rate of 1 ml/min. The acid output in the perfusate was determined at 5 minutes interval by titration with 0.02 M NaOH to pH 5.0. After the determination of basal acid secretion for 30 min, the acid secretion was stimulated by a continuous intravenous infusion of pentagastrin (16 µg/kg/h). The test compounds were administered by an intravenous bolus injection or intraduodenal administration after the stimulated acid secretion reached a plateau phase. The acid secretion was monitored after the administration.

The activity was evaluated either inhibition of total acid secretion from 0 hours to 1.5 or 3.5 hours after administration or the maximum inhibition after administration.

Inhibition of Gastric Acid Secretion in the Heidenhain Pouch Dog

Male Beagle dogs weighing 7-15 kg with Heidenhain pouch [Heidenhain R: *Arch Ges Physiol.* 1879; 19: 148-167] were used. The animals were allowed to recover from surgery for at least three weeks before the experiments. The animals were kept at a 12 hour light-dark rhythm, housed singly. They received standard food once daily at 11:00 a.m. and tap water ad libitum, and were fasted overnight prior to the experiment, with free access to water. Gastric juice samples were collected throughout the experiment by gravity drainage every 15 min. Acidity in the gastric juice was measured by titration to the end point of pH 7.0. Acid secretion was stimulated by a continuous intravenous infusion of histamine (80 µg/kg/h). Oral or intravenous bolus administration of the test compounds was done 90 minutes after commencement of the histamine infusion. The acid secretion was monitored after the administration. The activity was evaluated by the maximum inhibition relative to the corresponding control value.

Human Dofetilide Binding

Human ether a-go-go related gene (HERG) transfected HEK293S cells were prepared and grown in-house. Cell paste of HEK-293 cells expressing the HERG product can be suspended in 10-fold volume of 50 mM Tris buffer adjusted at pH 7.5 at 25° C. with 2 M HCl containing 1 mM MgCl$_2$, 10 mM KCl. The cells were homogenized using a Polytron homogenizer (at the maximum power for 20 seconds) and centrifuged at 48,000 g for 20 minutes at 4° C. The pellet was resuspended, homogenized and centrifuged once more in the same manner. The resultant supernatant was discarded and the final pellet was resuspended. (10-fold volume of 50 mM Tris buffer) and homogenized at the maximum power for 20 seconds. The membrane homogenate was aliquoted and stored at −80° C. until use. An aliquot was used for protein concentration determination using a Protein Assay Rapid Kit (wako) and Spectra max plate reader (Wallac). All the manipulation, stock solution and equipment were kept on ice at all times. For saturation assays, experiments were conducted in a total volume of 200 µl. Saturation was determined by incubating 36 µl of [$^3$H]-dofetilide, and 160 µl of membrane homogenates (20-30 µg protein per well) for 60 minutes at room temperature in the absence or presence of 10 µM dofetilide at final concentrations (4 μl) for total or nonspecific binding, respectively. All incubations were terminated by rapid vacuum filtration over PEI soaked glass fiber filter papers using Skatron cell harvester followed by two washes with 50 mM Tris buffer (pH 7.4 at 25° C.). Receptor-bound radioactivity was quantified by liquid scintillation counting using Packard LS counter.

For the competition assay, compounds were diluted in 96 well polypropylene plates as 4-point dilutions in semi-log format. All dilutions were performed in DMSO first and then transferred into 50 mM Tris buffer (pH 7.4 at 25° C.) containing 1 mM $MgCl_2$, 10 mM KCl so that the final DMSO concentration became equal to 1%. Compounds were dispensed in triplicate in assay plates (4 μl). Total binding and nonspecific binding wells were set up in 6 wells as vehicle and 10 μM dofetilide at final concentration, respectively. The radioligand was prepared at 5.6× final concentration and this solution was added to each well (36 μl). The assay was initiated by addition of YSi poly-L-lysine SPA beads (50 μl, 1 mg/well) and membranes (110 μl, 20 μg/well). Incubation was continued for 60 minutes at room temperature. Plates were incubated for a further 3 hours at room temperature for beads to settle. Receptor-bound radioactivity was quantified by counting Wallac MicroBeta plate counter.

Half-Life in Human Liver Microsomes (HLM)

Test compounds (1 μM) were incubated with 1 mM $MgCl_2$, 1 mM NADP+, 5 mM isocitric acid, 1 U/mL isocitric dehydrogenase and 0.8 mg/mL HLM in 100 mM potassium phosphate buffer (pH 7.4) at 37° C. on a number of 384-well plates. At several time points, a plate was removed from the incubator and the reaction was terminated with two incubation volumes of acetonitrile. The compound concentration in supernatant was measured by LC/MS/MS system. The intrinsic clearance value was calculated using following equations:

$$Cl_{int}(ul/min/mg\ protein) = \frac{k \times incubation\ volume}{Protein\ concentration}$$

Where, k=−slope of ln(concentration) vs. time (min-1)

hERG Patch Clamp Assay

To determine the potential of compounds to inhibit the hERG channel, the cloned counterpart of the rapidly inactivating delayed rectifier potassium current (IKr).

HEK293 cells stably expressing the hERG channel were used in whole-cell patch clamp electrophysiology studies at ambient temperature (26.5-28.5° C.). The methodology for stable transfection of this channel in HEK293 cells can be found elsewhere (Zhou et al 1998, Biophysical Journal, 74, pp 230-241). The solutions used for experimentation were standard extracellular solution of the following composition (mM); NaCl, 137; KCl, 4; $CaCl_2$, 1.8; $MgCl_2$, 1; Glucose, 10; HEPES, 10; pH 7.4±0.05 with NaOH/HCl; and standard intracellular solution of the following composition (mM); KCl, 130; $MgCl_2$, 1; HEPES, 10; EGTA, 5; MgATP, 5; pH 7.2±0.05 with KOH. The voltage protocol applied was designed to activate the hERG channel and allow the measurement of drug block of the channel and is as follows. First the membrane potential was stepped from a holding potential of −80 mV to +30 mV for 1 s. This was followed by a descending voltage ramp at a rate of 0.5 mV/ms back to holding potential of −80 mV and the peak outward current observed during the repolarizing ramp was measured. This protocol was evoked repeatedly every 4 seconds (0.25 Hz). After establishing a stable baseline period in the presence of vehicle (0.1% v/v DMSO), four increasing concentrations of test compound were then bath-applied sequentially until the response reached steady-state or 10 minutes (whichever occurred first). 10 micromol/L dofetilide was used at the end of each experiment as an internal positive control and to define maximum block.

Bioavailability in Rat

Adult rats of the Sprague-Dawley strain were used. One to two days prior to the experiments all rats were prepared by cannulation of the right jugular vein under anesthesia. The cannula was exteriorized at the nape of the neck. Blood samples (0.2-0.3 mL) were drawn from the jugular vein at intervals up to 24 hours after intravenous or oral administrations of the test compound. The samples were frozen until analysis. Bioavailability was assessed by calculating the quotient between the area under plasma concentration curve (AUC) following oral administration or intravenous administration.

Bioavailability in Dog

Adult Beagle dogs were used. Blood samples (0.2-0.5 mL) were drawn from the cephalic vein at intervals up to 24 hours after intravenous or oral administrations of the test compound. The samples were frozen until analysis. Bioavailability was assessed by calculating the quotient between the area under plasma concentration curve (AUC) following oral administration or intravenous administration.

Plasma Protein Binding

Plasma protein binding of the test compound (1 μM) was measured by the method of equilibrium dialysis using 96-well plate type equipment. Spectra-Por®, regenerated cellulose membranes (molecular weight cut-off 12,000-14,000, 22 mm×120 mm) were soaked for over night in distilled water, then for 20 minutes in 30% ethanol, and finally for 15 minutes in dialysis buffer (Dulbecco's phosphate buffered saline, pH7.4). Frozen plasma of human, Sprague-Dawley rats, and Beagle dogs were used. The dialysis equipment was assembled and added 150 μL of compound-fortified plasma to one side of each well and 150 μL of dialysis buffer to the other side of each well. After 4 hours incubation at 37° C. for 150 r.p.m, aliquots of plasma and buffer were sampled. The compound in plasma and buffer were extracted with 300 μL of acetonitrile containing internal standard compounds for analysis. The concentration of the compound was determined with LC/MS/MS analysis.

The fraction of the compound unbound was calculated by the following equation:

$$fu=1-\{([plasma]_{eq}-[buffer]_{eq})/([plasma]_{eq})\}$$

wherein $[plasma]_{eq}$ and $[buffer]_{eq}$ are the concentrations of the compound in plasma and buffer, respectively.

EXAMPLES

The following examples are provided for the purpose of further illustration only and are not intended to be limitations on the disclosed invention. Unless stated on otherwise in the following examples, general experimental conditions are as follows: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ pre-coated TLC plates or Merck $NH_2$ gel (an amine coated silica gel) F$_{254s}$ precoated TLC plates), mass spectrometry, nuclear magnetic resonance spectra (NMR), infrared absorption spectra (IR) or microanalysis. Yields are given for illustrative purposes only. Flash column chromatography was carried out using Biotage KP-SIL (40-63 μm), Biotage KP-NH (an amine coated silica gel) (40-75 μM), Fuji Silysia amino gel (30-50 μm) or Wako silica gel 300HG (40-60 μM). Microwave reactions were carried out using Personal Chemistry Emrys™ Optimizer or Biotage Initiator™. Preparative TLC was carried out using Merck silica gel 60 F$_{254}$ precoated TLC plates (0.5 or 1.0 mm thickness). All Mass data was obtained in Low-resolution mass spectral data (ESI) using ZMD™ or ZQ™ (Waters) and mass spectrometer. NMR data were determined at 270 MHz (JEOL JNM-LA 270 spectrometer) or 300 MHz (JEOL JNM-LA300 spectrometer) using deuterated chloroform (99.8%) or dimethylsulfoxide (99.9%) as solvent unless indicated otherwise, relative to tetramethylsilane (TMS) as internal standard in parts per million (ppm); conventional abbreviations used are: s=singlet, d=doublet, m=multiplet, dd=doublet of doublet, sep=septet, br.s=broad singlet, br.d=broad doublet, etc. IR spectra were measured by a Fourier transform infrared spectrophotometer (Shimazu FTIR-8300). Optical rotations were measured using a P-1020 Digital Polarimeter (JASCO Corporation).

Example 1

1-(2-Methoxyethyl)-N,N,2-trimethyl-8-phenyl-1,6,7, 8-tetrahydrochromeno[7,8-d]imidazole-5-carboxamide

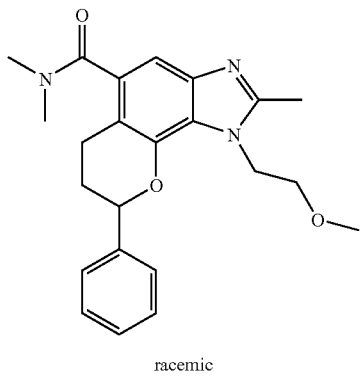

racemic

STEP 1:
N-[2-(Benzyloxy)-4-bromo-6-nitrophenyl]acetamide

To a solution of 2-(benzyloxy)-4-bromo-6-nitroaniline (33.0 g, 102 mmol, WO 2004054984) and acetic anhydride (14.5 mL, 153 mmol) in acetic acid (90 mL) was added concentrated sulfuric acid (2 drops) at 70° C. The mixture was stirred at 70° C. for 20 minutes. After cooling to room temperature, water (800 mL) was added, and the formed precipitate was collected by filtration and washed with diisopropyl ether to afford the title compound as a brown solid (30.9 g, 83%).
$^1$H NMR (CDCl$_3$, 270 MHz) δ: 7.69 (d, J=2.0 Hz, 1H), 7.56 (brs, 1H), 7.47-7.38 (m, 5H), 7.34 (d, J=2.0 Hz, 1H), 5.14 (s, 2H), 2.16 (s, 3H) ppm.
MS (ESI) m/z: 365 (M+H)$^+$.

STEP 2: N-[2-(Benzyloxy)-4-bromo-6-nitrophenyl]-N-(2-methoxyethyl)acetamide

To a suspension of sodium hydride (60% dispersion in mineral oil, 1.78 g, 44.5 mmol) in N,N-dimethylformamide (100 mL) was added dropwise a solution of N-[2-(benzyloxy)-4-bromo-6-nitrophenyl]acetamide (13.5 g, 37.1 mmol, Step 1) in N,N-dimethylformamide at 0° C. over 10 minutes. After stirring at 0° C. for 20 minutes, 1-bromo-2-methoxyethane (7.21 g, 51.9 mmol) was added, and the mixture was stirred at 50° C. for 2 hours. After cooling to room temperature, the mixture was poured onto water, and the aqueous layer was extracted with ethyl acetate/toluene (3:1). The combined organic layer was dried over magnesium sulfate and concentrated in vacuo. The residue was purified by column chromatography on silica gel eluting with hexane/ethyl acetate (3:1) to afford the title compound as a gray solid (12.1 g, 77%).
$^1$H NMR (CDCl$_3$, 270 MHz) δ: 7.70 (d, J=2.6 Hz, 1H), 7.45-7.32 (m, 6H), 5.22-5.10 (m, 2H), 4.23-4.13 (m, 1H), 3.51-3.34 (m, 2H), 3.24-3.13 (m, 1H), 3.09 (s, 3H), 1.89 (s, 3H) ppm. (Signals of other rotamers were also observed)
MS (ESI) m/z: 423 (M+H)$^+$.

STEP 3: 7-(Benzyloxy)-5-bromo-1-(2-methoxyethyl)-2-methyl-1H-benzimidazole

A mixture of N-[2-(benzyloxy)-4-bromo-6-nitrophenyl]-N-(2-methoxyethyl)acetamide (11.7 g, 27.7 mmol, Step 2) and iron powder (7.74 g, 139 mmol) in acetic acid (150 mL) was refluxed with stirring for 5 hours. After cooling to room temperature, the mixture was filtered through a pad of Celite, and the filtrate was concentrated in vacuo. The residue was poured onto water, and the aqueous layer was extracted with ethyl acetate. The combined organic layer was washed with brine, dried over magnesium sulfate, and concentrated in vacuo. The residue was purified by column chromatography on silica gel eluting with hexane/ethyl acetate (gradient elution from 2:1 to 1:1) to afford the title compound as a pale green solid (9.74 g, 93%).
$^1$H NMR (CDCl$_3$, 270 MHz) δ: 7.47-7.37 (m, 6H), 6.89 (d, J=1.3 Hz, 1H), 5.14 (s, 2H), 4.39 (t, J=5.3 Hz, 2H), 3.57 (t, J=5.3 Hz, 2H), 3.16 (s, 3H), 2.57 (s, 3H) ppm.

STEP 4: 7-(Benzyloxy)-1-(2-methoxyethyl)-2-methyl-1H-benzimidazole-5-carbonitrile A mixture of 7-(benzyloxy)-5-bromo-1-(2-methoxyethyl)-2-methyl-1H-benzimidazole (1.00 g, 2.66 mmol, Step 3), zinc cyanide (376 mg, 3.20 mmol), and tetrakis(triphenylphosphine)palladium (154 mg, 0.13 mmol) in N,N-dimethylformamide (15 mL) was stirred at 90° C. for 3 hours under nitrogen gas. After cooling to room temperature, the mixture was poured onto saturated potassium carbonate aqueous solution (100 mL), and the aqueous layer was extracted with ethyl acetate. The combined organic layer was dried over magnesium sulfate, and concentrated in vacuo. The residual solid was washed with ethyl acetate/diisopropyl ether (1:2) to afford the title compound as a white solid (648 mg, 76%).
$^1$H NMR (CDCl$_3$, 270 MHz) δ: 7.67 (br.s, 1H), 7.45-7.38 (m, 5H), 6.96 (br.s, 1H), 5.19 (s, 2H), 4.45 (t, J=5.3 Hz, 2H), 3.60 (t, J=4.6 Hz, 2H), 3.19 (s, 3H), 2.61 (s, 3H) ppm.
MS (ESI) m/z: 322 (M+H)$^+$.

STEP 5: 7-(Benzyloxy)-1-(2-methoxyethyl)-2-methyl-1H-benzimidazole-5-carboxylic acid A solution of 7-(benzyloxy)-1-(2-methoxyethyl)-2-methyl-1H-benzimidazole-5-carbonitrile (549 mg, 1.71 mmol, Step 4) and potassium hydroxide (85%, 564 mg, 8.54 mmol) in ethylene glycol (10 mL) was stirred at 135° C. for 5 hours. After cooling to room temperature, 2 mol/L hydrochloric acid was added until pH of the solution became about 3. The formed precipitate was collected by filtration to afford the title compound as a gray solid (530 mg, 91%).

$^1$H NMR (DMSO-d$_6$, 270 MHz) δ: 7.77 (br.s, 1H), 7.56-7.49 (m, 2H), 7.47-7.33 (m, 4H), 5.30 (s, 2H), 4.47, (t, J=5.3 Hz, 2H), 3.60 (t, J=5.3 Hz, 2H), 3.17 (s, 3H), 2.52 (s, 3H) ppm. (COOH was not observed)

MS (ESI) m/z: 341 (M+H)$^+$, 339 (M−H)$^−$.

STEP 6: Methyl 7-(benzyloxy)-1-(2-methoxyethyl)-2-methyl-1H-benzimidazole-5-carboxylate To a suspension of 7-(benzyloxy)-1-(2-methoxyethyl)-2-methyl-1H-benzimidazole-5-carboxylic acid (10.0 g, 29.4 mmol, Step 5) in methanol was added dropwise thionyl chloride (8.57 mL, 118 mmol) at room temperature, and the mixture was refluxed with stirring for 2 hours. After cooling to room temperature, the solvent was evaporated in vacuo. The residue was poured onto saturated sodium hydrogencarbonate aqueous solution, and the aqueous layer was extracted with dichloromethane. The combined organic layer was dried over magnesium sulfate, and concentrated in vacuo. The residue was suspended in diisopropyl ether (100 mL), and the precipitate was collected by filtration to afford the title compound as a gray solid (9.22 g, 85%).

$^1$H NMR (CDCl$_3$, 270 MHz) δ: 8.06 (s, 1H), 7.51 (s, 1H), 7.48-7.35 (m, 5H), 5.23 (s, 2H), 4.45 (t, J=5.3 Hz, 2H), 3.94 (s, 3H), 3.61 (t, J=5.3 Hz, 2H), 3.17 (s, 3H), 2.60 (s, 3H) ppm.

MS (ESI) m/z: 355 (M+H)$^+$.

STEP 7: Methyl 7-hydroxy-1-(2-methoxyethyl)-2-methyl-1H-benzimidazole-5-carboxylate A mixture of methyl 7-(benzyloxy)-1-(2-methoxyethyl)-2-methyl-1H-benzimidazole-5-carboxylate (9.21 g, 26.0 mmol, Step 6) and 10% palladium on carbon (500 mg) in methanol (150 mL) was stirred under hydrogen gas (4 atm) for 5 hours. The resulting mixture was filtered through a pad of Celite, and the filtrate was concentrated in vacuo. The residue was suspended in diisopropyl ether (150 mL), and the precipitate was collected by filtration to afford the title compound as a gray solid (6.35 g, 92%).

$^1$H NMR (CDCl$_3$, 270 MHz) δ: 10.31 (br.s, 1H), 7.62 (s, 1H), 7.24 (s, 1H), 4.49 (t, J=4.6 Hz, 2H), 3.83 (s, 3H), 3.68 (t, J=5.3 Hz, 2H), 3.21 (s, 3H) ppm.

MS (ESI) m/z: 266 (M+H)$^+$, 264 (M−H)$^−$.

STEP 8: Methyl 6-[(dimethylamino)methyl]-7-hydroxy-1-(2-methoxyethyl)-2-methyl-1H-benzimidazole-5-carboxylate The title compound was prepared as a white solid in 42% yield from methyl 7-hydroxy-1-(2-methoxyethyl)-2-methyl-1H-benzimidazole-5-carboxylate (3.00 g, Step 7) by the same manner in Step 3 of Example 5.

$^1$H NMR (CDCl$_3$, 270 MHz) δ: 7.72 (s, 1H), 4.54 (t, J=5.3 Hz, 2H), 4.24 (s, 2H), 3.88 (s, 3H), 3.76 (t, J=5.3 Hz, 2H), 3.27 (s, 3H), 2.59 (s, 3H), 2.38 (s, 6H) ppm. (OH was not observed)

MS (ESI) m/z: 322 (M+H)$^+$, 320 (M−H)$^−$.

STEP 9: Methyl 7-hydroxy-1-(2-methoxyethyl)-2-methyl-6-(3-oxo-3-phenylpropyl)-1H-benzimidazole-5-carboxylate A mixture of methyl 6-[(dimethylamino)methyl]-7-hydroxy-1-(2-methoxyethyl)-2-methyl-1H-benzimidazole-5-carboxylate (2.04 g, 6.35 mmol, Step 8) and 1-(1-phenylvinyl)pyrrolidine (1.43 g, 8.25 mmol, J. Am. Chem. Soc., 1994, 116, 5985-5986.) in toluene (80 mL) was stirred at 100° C. for 3 hours. After cooling to room temperature, the solvent was removed in vacuo. The residue was purified by column chromatography on silica gel eluting with dichloromethane/methanol (30:1) to afford the title compound as a brown amorphous (2.08 g, 82%).

$^1$H NMR (CDCl$_3$, 270 MHz) δ: 9.72 (s, 1H), 8.03 (d, J=7.2 Hz, 2H), 7.95 (s, 1H), 7.59 (t, J=7.9 Hz, 1H), 7.46 (t, J=7.9 Hz, 2H), 4.61 (t, J=5.3 Hz, 2H), 3.92 (s, 3H), 3.83-3.73 (m, 4H), 3.41 (t, J=5.3 Hz, 2H), 3.29 (s, 3H), 2.60 (s, 3H) ppm.

MS (ESI) m/z: 397 (M+H)$^+$, 395 (M−H)

STEP 10: Methyl 7-hydroxy-6-(3-hydroxy-3-phenylpropyl)-1-(2-methoxyethyl)-2-methyl-1H-benzimidazole-5-carboxylate To a solution of methyl 7-hydroxy-1-(2-methoxyethyl)-2-methyl-6-(3-oxo-3-phenylpropyl)-1H-benzimidazole-5-carboxylate (2.08 g, 5.25 mmol, Step 9) in ethanol (50 mL) was added sodium borohydride (298 mg, 7.87 mmol) at room temperature. After stirring at the same temperature for 4 hours, the solvent was evaporated, and the residue was poured onto saturated sodium hydrogencarbonate aqueous solution, and the aqueous layer was extracted with ethyl acetate. The combined organic layer was dried over magnesium sulfate, and concentrated in vacuo. The residue was purified by column chromatography on silica gel eluting with dichloromethane/methanol (20:1) to afford the title compound as a brown amorphous (2.08 g, 99%).

$^1$H NMR (CDCl$_3$, 270 MHz) δ: 8.56 (br, 1H), 7.88 (br.s, 1H), 7.35-7.25 (m, 5H), 4.66 (dd, J=3.3 and 11.2 Hz, 1H), 4.63-4.45 (m, 2H), 3.85 (s, 3H), 3.80-3.71 (m, 2H), 3.31 (s, 3H), 3.40-3.20 (m, 2H), 2.58 (s, 3H), 2.40-2.24 (m, 1H), 2.17-2.02 (m, 1H) ppm. (OH was not observed)

MS (ESI) m/z: 399 (M+H)$^+$, 397 (M−H)$^−$.

STEP 11: Methyl 1-(2-methoxyethyl)-2-methyl-8-phenyl-1,6,7,8-tetrahydrochromeno[7,8-d]imidazole-5-carboxylate A suspension of methyl 7-hydroxy-6-(3-hydroxy-3-phenylpropyl)-1-(2-methoxyethyl)-2-methyl-1H-benzimidazole-5-carboxylate (2.00 g, 5.01 mmol, Step 10) in 85% phosphoric acid (40 mL) was stirred at 80° C. for 20 minutes. After cooling to room temperature, the mixture was poured onto ice-water (300 mL), and the solution was neutralized by 10 N sodium hydroxide aqueous solution. The aqueous layer was extracted with dichloromethane. The combined organic layer was dried over magnesium sulfate, and concentrated in vacuo. The residue was purified by column chromatography on silica gel eluting with ethyl acetate/methanol (gradient elution from ethyl acetate only to 20:1) to afford the title compound as a pale brown solid (1.47 g, 77%).

$^1$H NMR (CDCl$_3$, 270 MHz) δ: 7.96 (s, 1H), 7.46-7.35 (m, 5H), 5.14 (dd, J=2.0 and 10.6 Hz, 1H), 4.50-4.39 (m, 2H), 3.90 (s, 3H), 3.65-3.58 (m, 2H), 3.39-3.31 (m, 2H), 3.17 (s, 3H), 2.59 (s, 3H), 2.39-2.28 (m, 1H), 2.20-2.04 (m, 1H) ppm.

MS (ESI) m/z: 381 (M+H)$^+$.

STEP 12: 1-(2-Methoxyethyl)-2-methyl-8-phenyl-1,6,7,8-tetrahydrochromeno[7,8-d]imidazole-5-carboxylic acid A mixture of methyl 1-(2-methoxyethyl)-2-methyl-8-phenyl-1,6,7,8-tetrahydrochromeno[7,8-d]imidazole-5-carboxylate (1.37 g, 3.61 mmol, Step 11), 2 mol/L sodium hydroxide aqueous solution (3.60 mL, 7.21 mmol), and ethanol (20 mL) was stirred at 80° C. for 2 hours. After cooling to room temperature, 2 mol/L hydrochloric acid (3.60 mL, 7.21 mmol) was added, and the formed precipitate was collected by filtration to afford the title compound as a white solid (1.28 g, 96%).

$^1$H NMR (DMSO-$d_6$, 300 MHz) δ: 12.52 (s, 1H), 7.69 (s, 1H), 7.52-7.32 (m, 5H), 5.24 (d, J=8.8 Hz, 1H), 4.45-4.38 (m, 2H), 3.62-3.55 (m, 2H), 3.26-3.18 (m, 2H), 3.13 (s, 3H), 2.34-2.22 (m, 1H), 2.09-1.92 (m, 1H) ppm.
MS (ESI) m/z: 367 (M+H)$^+$, 365 (M−H)$^-$.

STEP 13: 1-(2-Methoxyethyl)-N,N,2-trimethyl-8-phenyl-1,6,7,8-tetrahydrochromeno[7,8-d]imidazole-5-carboxamide To a solution of 1-(2-methoxyethyl)-2-methyl-8-phenyl-1,6,7,8-tetrahydrochromeno[7,8-d]imidazole-5-carboxylic acid (200 mg, 0.55 mmol, Step 12), triethylamine (0.30 mL, 2.18 mmol), and O-benzotriazol-1-yl-N,N,N',N'-tetramethyluronium hexafluorophosphate (228 mg, 0.60 mmol) in N,N-dimethylformamide (5 mL) was added dimethylamine hydrochloride (49 mg, 0.60 mmol) at 0° C. After stirring at room temperature for 12 h, the mixture was poured onto water, and the aqueous layer was extracted with dichloromethane. The combined organic layer was dried over magnesium sulfate and concentrated in vacuo. The residue was purified by column chromatography on silica gel eluting with dichloromethane/methanol (20:1) to afford the title compound as a white amorphous (215 mg, quant.).

$^1$H NMR (CDCl$_3$, 300 MHz) δ: 7.45-7.35 (m, 5H), 7.14 (s, 1H), 5.16 (dd, J=2.2 and 10.3 Hz, 1H), 4.52-4.35 (m, 2H), 3.69-3.58 (m, 2H), 3.18 (s, 3H), 3.15 (s, 3H), 3.2-2.7 (m, 2H), 2.90 (s, 3H), 2.58 (s, 3H), 2.40-2.10 (m, 2H) ppm.
MS (ESI) m/z: 394 (M+H)$^+$.

Example 2

(+)-1-(2-Methoxyethyl)-N,N,2-trimethyl-8-phenyl-1,6,7,8-tetrahydrochromeno[7,8-d]imidazole-5-carboxamide and

Example 3

(−)-1-(2-Methoxyethyl)-N,N,2-trimethyl-8-phenyl-1,6,7,8-tetrahydrochromeno[7,8-d]imidazole-5-carboxamide The fraction-1 (68 mg) and fraction-2 (68 mg) were prepared from racemic 1-(2-methoxyethyl)-N,N,2-trimethyl-8-phenyl-1,6,7,8-tetrahydrochromeno[7,8-d]imidazole-5-carboxamide (200 mg, Step 13 in Example 1) by HPLC as follows.

Isolation Condition
Column: CHIRALPAK AD-H (20 mm×250 mm, DAICEL)
Mobile phase: n-Hexane/Ethanol/Diethylamine (90/10/0.1)
Flow rate: 20 mL/min (+)-1-(2-Methoxyethyl)-N,N,2-trimethyl-8-phenyl-1,6,7,8-tetrahydrochromeno[7,8-d]imidazole-5-carboxamide (fraction-1)

$^1$H NMR: spectrum data were identical with those of the racemate
optical rotation: $[α]_D^{25}$=+54.3° (c=0.31, Methanol)
retention time: 33 min (−)-1-(2-Methoxyethyl)-N,N,2-trimethyl-8-phenyl-1,6,7,8-tetrahydrochromeno[7,8-d]imidazole-5-carboxamide (fraction-2)

$^1$H NMR: spectrum data were identical with those of the racemate
optical rotation: $[α]_D^{25}$=−59.1° (c=0.30, Methanol)
retention time: 39 min

Example 4

N-(2-Hydroxyethyl)-1-(2-methoxyethyl)-N,2-dimethyl-8-phenyl-1,6,7,8-tetrahydrochromeno[7,8-d]imidazole-5-carboxamide

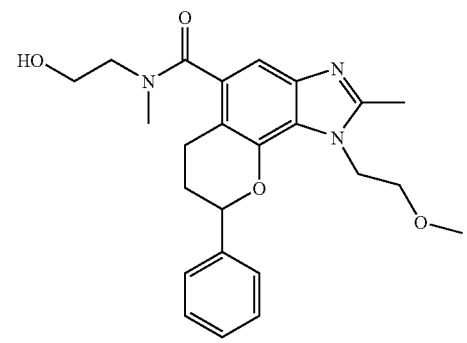 [SMILES: COCCn1c(C)nc2cc(C(=O)N(C)CCO)c3c(c21)OC(c1ccccc1)CC3]

The title compound was prepared as a white solid in quantitative yield from 1-(2-methoxyethyl)-2-methyl-8-phenyl-1,6,7,8-tetrahydrochromeno[7,8-d]imidazole-5-carboxylic acid (200 mg, 0.55 mmol, Step 12 of Example 1) and 2-(methylamino)ethanol (45 mg, 0.60 mmol) by the same manner in Step 13 of Example 1.

$^1$H NMR (CDCl$_3$, 300 MHz) δ: 7.48-7.33 (m, 5H), 7.14 (s, 1H), 5.16 (d, J=10.3 Hz, 1H), 4.50-4.40 (m, 2H), 3.98-3.89 (m, 2H), 3.72-3.60 (m, 2H), 3.26-3.15 (m, 2H), 3.2-2.7 (m, 2H), 3.19 (s, 3H), 2.96 (s, 3H), 2.59 (s, 3H), 2.35-1.80 (m, 2H) ppm. (OH was not observed)
MS (ESI) m/z: 424 (M+H)$^+$.

Example 5

8-(4-Fluorophenyl)-1-(2-methoxyethyl)-N,N,2-trimethyl-1,6,7,8-tetrahydrochromeno[7,8-d]imidazole-5-carboxamide

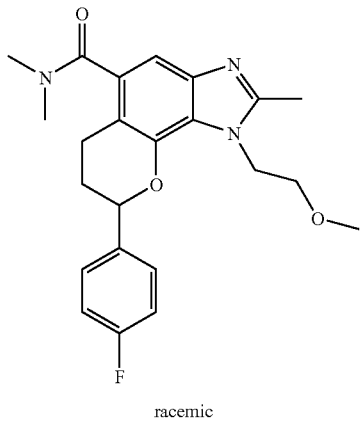

racemic

STEP 1: 7-(Benzyloxy)-1-(2-methoxyethyl)-N,N,2-trimethyl-1H-benzimidazole-5-carboxamide A mixture of 7-(benzyloxy)-1-(2-methoxyethyl)-2-methyl-1H-benzimidazole-5-carboxylic acid (520 mg, 1.53 mmol, Step 5 of Example 1), dimethylamine hydrochloride (374 mg, 4.58 mmol), 1-[3-(dimethylamino)propyl]-3-ethylcarbodiimide hydrochloride (498 mg, 2.60 mmol), 1-hydroxybenzotriazole hydrate (413 mg, 3.06 mmol), and triethylamine (0.64 mL, 4.58 mmol) in N,N-dimethylformamide (10 mL) was stirred at room temperature for 1 day. The mixture was poured onto water, and the aqueous layer was extracted with ethyl acetate. The combined organic layer was dried over magnesium sulfate, and concentrated in vacuo. The residue was purified by column chromatography on silica gel eluting with dichloromethane/methanol (10:1) to afford the title compound as a white solid (524 mg, 93%).

$^1$H NMR (CDCl$_3$, 270 MHz) δ: 7.46-7.33 (m, 6H), 6.94 (br.s, 1H), 5.20 (s, 2H), 4.44 (t, J=5.3 Hz, 2H), 3.61 (t, J=5.3 Hz, 2H), 3.17 (s, 3H), 3.09 (br.s, 6H), 2.59 (s, 3H) ppm.

MS (ESI) m/z: 368 (M+H)$^+$.

STEP 2: 7-Hydroxy-1-(2-methoxyethyl)-N,N,2-trimethyl-1H-benzimidazole-5-carboxamide A mixture of 7-(benzyloxy)-1-(2-methoxyethyl)-N,N,2-trimethyl-1H-benzimidazole-5-carboxamide (483 mg, 1.31 mmol, Step 1) and 10% palladium-carbon (50 mg) in ethanol (30 mL) was stirred under hydrogen gas for 19 hours. The resulting mixture was filtered through a pad of Celite, and the filtrate was concentrated in vacuo to afford the title compound as a white solid (347 mg, 95%).

$^1$H NMR (CDCl$_3$, 300 MHz) δ: 9.57 (br.s, 1H), 7.14 (d, J=1.5 Hz, 1H), 6.93 (d, J=1.5 Hz, 1H), 4.43 (t, J=5.1 Hz, 2H), 3.64 (t, J=5.1 Hz, 2H), 3.20 (s, 3H), 3.15 (br.s, 3H), 3.05 (br.s, 3H), 2.53 (s, 3H) ppm.

MS (ESI) m/z: 278 (M+H)$^+$.

STEP 3: 6-[(Dimethylamino)methyl]-7-hydroxy-1-(2-methoxyethyl)-N,N,2-trimethyl-1H-benzimidazole-5-carboxamide To a stirred solution of 7-hydroxy-1-(2-methoxyethyl)-N,N,2-trimethyl-1H-benzimidazole-5-carboxamide (1.0 g, 3.6 mmol, Step 2) and potassium carbonate (748 mg, 5.4 mmol) in N,N-dimethylformamide (36 mL) at 0° C. was added N,N-dimethylmethyleneiminium iodide (867 mg, 4.7 mmol). After stirring at the same temperature for 4 hours, the reaction mixture was quenched with saturated sodium hydrogencarbonate aqueous solution and extracted with dichloromethane. The combined organic layer was washed with brine, dried over magnesium sulfate, and concentrated in vacuo. The residue was purified by column chromatography on NH-gel eluting with ethyl acetate/methanol (30:1) to afford the title compound (855 mg, 71%) as a white amorphous.

$^1$H NMR (CDCl$_3$, 270 MHz) δ: 6.97 (s, 1H), 4.51 (t, J=5.3 Hz, 2H), 3.65-3.82 (br.s, 2H), 3.75 (t, J=5.3 Hz, 2H), 3.27 (s, 3H), 3.14 (s, 3H), 2.88 (s, 3H), 2.58 (s, 3H), 2.36 (s, 6H) ppm. (OH was not observed)

MS (ESI) m/z: 335 (M+H)$^+$.

STEP 4: 6-[3-(4-Fluorophenyl)-3-oxopropyl]-7-hydroxy-1-(2-methoxyethyl)-N,N,2-trimethyl-1H-benzimidazole-5-carboxamide The title compound was prepared as a brown amorphous in 86% yield from 6-[(dimethylamino)methyl]-7-hydroxy-1-(2-methoxyethyl)-N,N,2-trimethyl-1H-benzimidazole-5-carboxamide (648 mg, 1.94 mmol, Step 3) and 1-[1-(4-fluorophenyl)vinyl]pyrrolidine (556 mg, 2.91 mmol, WO9940091) by the same manner in Step 9 of Example 1.

$^1$H NMR (CDCl$_3$, 270 MHz) δ: 9.38 (s, 1H), 8.05 (dd, J=8.6, 5.3 Hz, 2H), 7.10 (t, J=8.6 Hz, 2H), 7.06 (s, 1H), 4.57 (t, J=5.3 Hz, 2H), 3.79 (t, J=5.3 Hz, 2H), 3.30 (s, 3H), 3.18 (s, 3H), 2.87 (s, 3H), 2.58 (s, 3H) ppm. (2×CH$_2$ were not observed)

MS (ESI) m/z: 428 (M+H)$^+$, 426 (M−H)$^−$.

STEP 5: 6-[3-(4-Fluorophenyl)-3-hydroxypropyl]-7-hydroxy-1-(2-methoxyethyl)-N,N,2-trimethyl-1H-benzimidazole-5-carboxamide The title compound was prepared as a brown amorphous in 87% yield from 6-[3-(4-fluorophenyl)-3-oxopropyl]-7-hydroxy-1-(2-methoxyethyl)-N,N,2-trimethyl-1H-benzimidazole-5-carboxamide (713 mg, 1.67 mmol, Step 4) by the same manner in Step 10 of Example 1.

$^1$H NMR (CDCl$_3$, 300 MHz) δ: 7.26 (m, 2H), 6.94 (t, J=8.8 Hz, 2H), 6.94 (s, 1H), 4.55-4.42 (m, 3H), 3.72 (br.s, 2H), 3.31 (s, 3H), 3.10 (s, 3H), 2.79 (s, 3H), 2.51 (s, 3H) ppm. (2×CH$_2$, and 2×OH were not observed)

MS (ESI) m/z: 430 (M+H)$^+$, 428 (M−H).

STEP 6: 8-(4-Fluorophenyl)-1-(2-methoxyethyl)-N,N,2-trimethyl-1,6,7,8-tetrahydrochromeno[7,8-d]imidazole-5-carboxamide The title compound was prepared as a white solid in 93% yield from 6-[3-(4-fluorophenyl)-3-hydroxypropyl]-7-hydroxy-1-(2-methoxyethyl)-N,N,2-trimethyl-1H-benzimidazole-5-carboxamide (273 mg, 0.636 mmol, Step 5) by the same manner in Step 11 of Example 1.

$^1$H NMR (CDCl$_3$, 300 MHz) δ: 7.40 (dd, J=8.8, 5.1 Hz, 2H), 7.14 (s, 1H), 7.11 (t, J=8.8 Hz, 2H), 5.12 (dd, J=10.3, 2.2 Hz, 1H), 4.48-4.33 (m, 2H), 3.64-3.57 (m, 2H), 3.2-2.7 (m, 2H), 3.19 (s, 3H), 3.15 (s, 3H), 2.90 (s, 3H), 2.57 (s, 3H), 2.29-2.11 (m, 2H) ppm.

MS (ESI) m/z: 412 (M+H)$^+$.

Example 6

(+)-8-(4-Fluorophenyl)-1-(2-methoxyethyl)-N,N,2-trimethyl-1,6,7,8-tetrahydrochromeno[7,8-d]imidazole-5-carboxamide and Example 7

(−)-8-(4-Fluorophenyl)-1-(2-methoxyethyl)-N,N,2-trimethyl-1,6,7,8-tetrahydrochromeno[7,8-d]imidazole-5-carboxamide The fraction-1 (73 mg) and fraction-2 (73 mg) were prepared from racemic 8-(4-fluorophenyl)-1-(2-methoxyethyl)-N,N,2-trimethyl-1,6,7,8-tetrahydrochromeno[7,8-d]imidazole-5-carboxamide (183 mg, STEP 6 in Example 5) by HPLC as follows.

Isolation Condition

Column: CHIRALCEL OJ-H (20 mm×250 mm, DAICEL)

Mobile phase: n-Hexane/2-Propanol/Diethylamine (88/12/0.1)

Flow rate: 18.9 mL/min (−)-8-(4-Fluorophenyl)-1-(2-methoxyethyl)-N,N,2-trimethyl-1,6,7,8-tetrahydrochromeno[7,8-d]imidazole-5-carboxamide (fraction-1)

$^1$H NMR: spectrum data were identical with those of the racemate optical rotation: $[α]_D^{24}$=−44.7° (c=0.31, Methanol)

retention time: 11 min (+)-8-(4-Fluorophenyl)-1-(2-methoxyethyl)-N,N,2-trimethyl-1,6,7,8-tetrahydrochromeno[7,8-d]imidazole-5-carboxamide (fraction-2)

$^1$H NMR: spectrum data were identical with those of the racemate optical rotation: $[α]_D^{24}$=+44.0° (c=0.30, Methanol)

retention time: 18 min

Example 8

8-(4-Fluorophenyl)-1-(3-hydroxypropyl)-N,N,2-trimethyl-1,6,7,8-tetrahydrochromeno[7,8-d]imidazole-5-carboxamide

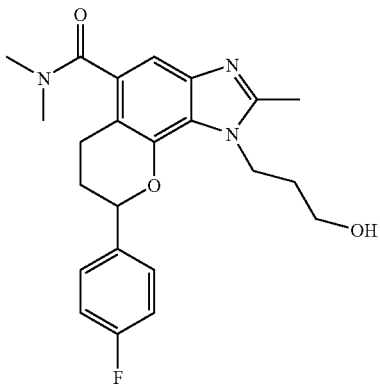 [SMILES: Cc1nc2cc(C(=O)N(C)C)c3c(c2n1CCCO)OC(c1ccc(F)cc1)CC3]

STEP 1: 4-(Benzyloxy)-6-bromo-2-methyl-1H-benzimidazole

A mixture of N-[2-(benzyloxy)-4-bromo-6-nitrophenyl]acetamide (120 g, 329 mmol, Step 1 of Example 1) and iron powder (55.1 g, 986 mmol) in acetic acid (500 mL) was refluxed with stirring for 6 hours. After cooling to room temperature, the mixture was filtered through a pad of Celite, and the filtrate was concentrated in vacuo. The residue was diluted with ethyl acetate (1.5 L). The resulted precipitates were filtered through a pad of Celite, and washed with ethyl acetate (500 mL). The filterate was concentrated in vacuo, and the residue was diluted with ethyl acetate (200 mL). The brine (800 mL) was added to the organic mixture, the resulted white precipitates were collected by filtration, and washed with water (200 mL) and diethyl ether (200 mL). The white solid was dissolved with dichloromethane/methanol (10:1, 1.0 L), dried over magnesium sulfate, and concentrated. The solid was triturated with diethyl ether (300 mL), collected by filtration, and dried in vacuo to afford the title compound as a white solid (54.7 g, 53%).

$^1$H NMR (DMSO-d$_6$, 270 MHz) δ: 7.63-7.28 (m, 7H), 5.38 (s, 2H), 2.69 (s, 3H) ppm. (NH was not observed.)

MS (ESI) m/z: 317 (M+H)$^+$, 315 (M−H)$^-$.

STEP 2: 4-(Benzyloxy)-6-bromo-2-methyl-1-[(4-methylphenyl)sulfonyl]-1H-benzimidazole To a suspension of 4-(benzyloxy)-6-bromo-2-methyl-1H-benzimidazole (79.2 g, 250 mmol, Step 1) in N,N-dimethylformamide (500 mL) was added sodium hydride (60% in mineral oil, 12.0 g, 300 mmol) at 0° C. After stirring at room temperature for 20 minutes, the reaction mixture was cooled to 0° C. To the mixture was added 4-methylbenzenesulfonyl chloride (47.6 g, 250 mmol) at 0° C., and the reaction mixture was stirred at room temperature for 30 minutes. The mixture was quenched with water, and the white precipitates were collected by filtration, washed with diisopropyl ether, and dried in vacuo at 70° C. for 7 hours to afford the title compound as a white solid (116 g, 98%).

¹H NMR (DMSO-d₆, 270 MHz) δ: 7.98 (d, J=8.1 Hz, 2H), 7.64 (d, J=1.9 Hz, 1H), 7.53-7.34 (m, 7H), 7.22 (d, J=1.9 Hz, 1H), 5.28 (s, 2H), 2.74 (s, 3H), 2.38 (s, 3H) ppm.
MS (ESI) m/z: 471 (M+H)⁺, 469 (M−H)⁻.

STEP 3: 4-(Benzyloxy)-N,N,2-trimethyl-1-[(4-methylphenyl)sulfonyl]-1H-benzimidazole-6-carboxamide A mixture of 4-(benzyloxy)-6-bromo-2-methyl-1-[(4-methylphenyl)sulfonyl]-1H-benzimidazole (53.0 g, 112 mmol, Step 2) and tetrakis(triphenylphosphine)palladium (25.9 g, 22.4 mmol) in 2 mol/L dimethylamine tetrahydrofuran solution (580 mL) was stirred at 65° C. under carbon monoxide gas (1 atm) for 32 hours. The mixture was cooled to room temperature, and diluted with ethyl acetate. The organic mixture was washed with saturated ammonium chloride aqueous solution and brine, dried over magnesium sulfate and concentrated in vacuum. The residue was purified by column chromatography on silica gel eluting with hexane/ethyl acetate (gradient elution from 1:2 to 1:3) to afford the title compound as a white solid (21.8 g, 42%).
¹H NMR (CDCl₃, 270 MHz) δ: 7.80 (d, J=8.1 Hz, 2H), 7.70 (s, 1H), 7.45 (d, J=8.1 Hz, 2H), 7.40-7.22 (m, 5H), 6.86 (s, 1H), 5.32 (s, 2H), 3.11 (br.s, 3H), 2.89 (br.s, 3H), 2.81 (s, 3H), 2.40 (s, 3H) ppm.
MS (ESI) m/z: 464 (M+H)⁺.

STEP 4: 4-Hydroxy-N,N,2-trimethyl-1-[(4-methylphenyl)sulfonyl]-1H-benzimidazole-6-carboxamide A mixture of 4-(benzyloxy)-N,N,2-trimethyl-1-[(4-methylphenyl)sulfonyl]-1H-benzimidazole-6-carboxamide (29.0 g, 62.6 mmol, Step 3) and 10% palladium on carbon (6.0 g) in tetrahydrofuran (200 mL) was stirred under hydrogen gas (1 atm) at room temperature for 24 hours. Another 4.0 g of 10% palladium on carbon was added, and the mixture was stirred under hydrogen gas (1 atm) at room temperature for additional 6 hours. The resulted mixture was filtered through a pad of Celite, and the filtrate was concentrated in vacuo to afford the title compound as a white solid (23.0 g, 98%).
¹H NMR (CDCl₃, 270 MHz) δ: 7.82 (d, J=8.1 Hz, 2H), 7.63 (s, 1H), 7.31 (d, J=8.1 Hz, 2H), 6.92 (s, 1H), 3.14 (br.s, 3H), 3.01 (br.s, 3H), 2.79 (s, 3H), 2.40 (s, 3H) ppm (—OH was not observed).
MS (ESI) m/z: 374 (M+H)⁺, 372 (M−H)⁻.

STEP 5: 5-[(Dimethylamino)methyl]-4-hydroxy-N,N,2-trimethyl-1-[(4-methylphenyl)sulfonyl]-1H-benzimidazole-6-carboxamide To a solution of 4-hydroxy-N,N,2-trimethyl-1-[(4-methylphenyl)sulfonyl]-1H-benzimidazole-6-carboxamide (1.00 g, 2.68 mmol, Step 4) in dichloromethane (50 mL) was added N,N-dimethylmethyleneiminium iodide (545 mg, 2.95 mmol) at room temperature and the mixture was stirred at 40° C. for 15 hours. The reaction was quenched by saturated sodium hydrogencarbonate aqueous solution. The mixture was extracted with dichloromethane. The organic layer was dried over sodium sulfate and concentrated in vacuo to afford the title compound as a yellow amorphous (1.04 g, 90%).
¹H NMR (CDCl₃, 270 MHz) δ: 7.78 (d, J=8.6 Hz, 2H), 7.35 (s, 1H), 7.32-7.24 (m, 2H), 3.83-3.56 (br, 2H), 3.17 (s, 3H), 2.87 (s, 3H), 2.77 (s, 3H), 2.40 (s, 3H), 2.36 (s, 6H) ppm. (OH was not observed)
MS (ESI) m/z: 431 (M+H)⁺, 429 (M−H)⁻.

STEP 6: 5-[3-(4-Fluorophenyl)-3-oxopropyl]-4-hydroxy-N,N,2-trimethyl-1-[(4-methylphenyl)sulfonyl]-1H-benzimidazole-6-carboxamide The title compound was prepared as a brown solid in 52% yield from 5-[(dimethylamino)methyl]-4-hydroxy-N,N,2-trimethyl-1-[(4-methylphenyl)sulfonyl]-1H-benzimidazole-6-carboxamide (1.15 g, Step 5) and 1-[1-(4-fluorophenyl)vinyl]pyrrolidine (766 mg, WO9940091) by the same manner in Step 9 of Example 1.
¹H NMR (CDCl₃, 270 MHz) δ: 8.02 (dd, J=8.8, 5.1 Hz, 2H), 7.79 (d, J=8.1 Hz, 2H), 7.44 (s, 1H), 7.34-7.24 (m, 2H), 7.08 (dd, J=8.8, 8.8 Hz, 2H), 3.18 (s, 3H), 2.87 (s, 3H), 2.76 (s, 3H), 2.39 (s, 3H) ppm. (OH and 2×CH₂ were not observed)
MS (ESI) m/z: 524 (M+H)⁺, 522 (M−H)⁻.

STEP 7: 5-[3-(4-Fluorophenyl)-3-hydroxypropyl]-4-hydroxy-N,N,2-trimethyl-1-[(4-methylphenyl)sulfonyl]-1H-benzimidazole-6-carboxamide The title compound was prepared as a brown solid in 64% yield from 5-[3-(4-fluorophenyl)-3-oxopropyl]-4-hydroxy-N,N,2-trimethyl-1-[(4-methylphenyl)sulfonyl]-1H-benzimidazole-6-carboxamide (300 mg, Step 6) by the same manner in Step 10 of Example 1.
¹H NMR (CDCl₃, 270 MHz) δ: 7.82 (d, J=8.6 Hz, 2H), 7.43 (s, 1H), 7.35-7.23 (m, 4H), 6.95 (dd, J=8.9, 8.9 Hz, 2H), 3.17 (s, 3H), 2.85 (s, 3H), 2.76 (s, 3H), 2.41 (s, 3H) ppm. (CH, 2×CH₂, and 2×OH were not observed)
MS (ESI) m/z: 526 (M+H)⁺, 524 (M−H)⁻.

STEP 8: 8-(4-Fluorophenyl)-N,N,2-trimethyl-3,6,7,8-tetrahydrochromeno[7,8-d]imidazole-5-carboxamide The title compound was prepared as a brown oil in 43% yield from 5-[3-(4-fluorophenyl)-3-hydroxypropyl]-4-hydroxy-N,N,2-trimethyl-1-[(4-methylphenyl)sulfonyl]-1H-benzimidazole-6-carboxamide (192 mg, Step 7) by the same manner in Step 11 of Example 1.
¹H NMR (CDCl₃, 270 MHz) δ: 7.43 (dd, J=8.6, 5.3 Hz, 2H), 7.40-7.19 (br, 3H), 3.14 (s, 3H), 2.92-2.84 (br, 3H), 2.59 (s, 3H) ppm. (CH, 2×CH₂, and NH were not observed)
MS (ESI) m/z: 354 (M+H)⁺, 352 (M−H).

STEP 9: 1-(3-{[tert-Butyl(dimethyl)silyl]oxy}propyl)-8-(4-fluorophenyl)-N,N,2-trimethyl-1,6,7,8-tetrahydrochromeno[7,8-d]imidazole-5-carboxamide To a solution of 8-(4-fluorophenyl)-N,N,2-trimethyl-3,6,7,8-tetrahydrochromeno[7,8-d]imidazole-5-carboxamide (52.0 mg, 0.147 mmol, Step 8) in N,N-dimethylformamide (1.5 mL), was added sodium hydride (7.1 mg, 0.18 mmol) at 0° C. and the mixture was stirred at 0° C. for 30 minutes. Then (3-bromopropoxy)(tert-butyl)dimethylsilane (48.4 mg, 0.191 mmol) was added to the mixture at 0° C. The mixture was allowed to warm to room temperature, stirred for 4 hours and left at the same temperature overnight. The reaction was quenched by saturated ammonium chloride aqueous solution. The mixture was extracted with ethyl acetate. The combined organic layers were washed with water and brine. It was dried over sodium sulfate and concentrated in vacuo. The residue was purified by preparative TLC eluting with hexane/ethyl acetate (1:1 and then 1:4) to afford the title compound as a brown oil (35.5 mg, 46%).

$^1$H NMR (CDCl$_3$, 270 MHz) δ: 7.41 (dd, J=8.6, 5.3 Hz, 2H), 7.16-7.06 (m, 3H), 5.11 (dd, J=10.2, 2.3 Hz, 1H), 4.31 (t, J=7.3 Hz, 2H), 3.41 (t, J=5.3 Hz, 2H), 3.2-2.7 (m, 2H), 3.15 (s, 3H), 2.90 (s, 3H), 2.57 (s, 3H), 2.37-2.02 (m, 2H), 1.90 (tt, J=6.6, 6.6 Hz, 2H), 0.88 (s, 9H), −0.01 (s, 6H) ppm.

MS (ESI) m/z: 526 (M+H)$^+$.

STEP 10: 8-(4-Fluorophenyl)-1-(3-hydroxypropyl)-N,N,2-trimethyl-1,6,7,8-tetrahydrochromeno[7,8-d]imidazole-5-carboxamide To the solution of 1-(3-{[tert-butyl(dimethyl)silyl]oxy}propyl)-8-(4-fluorophenyl)-N,N,2-trimethyl-1,6,7,8-tetrahydrochromeno[7,8-d]imidazole-5-carboxamide (35 mg, 0.067 mmol, Step 9) in tetrahydrofuran was added 1M solution of tetrabutylammonium fluoride in tetrahydrofuran (0.1 mL). The mixture was stirred at room temperature for 2.5 hours. The reaction was quenched by saturated ammonium chloride aqueous solution. The mixture was extracted with ethyl acetate. The combined organic layers were washed with water and brine, dried over sodium sulfate, and concentrated in vacuo. The residue was purified by preparative TLC eluting with dichloromethane/methanol (20:1). The obtained product was triturated in hexane to afford the title compound as a pale yellow solid (8.6 mg, 31%)

$^1$H NMR (CDCl$_3$, 270 MHz) δ: 7.43 (dd, J=9.2, 5.3 Hz, 2H), 7.16-7.06 (m, 3H), 5.12 (dd, J=10.2, 2.3 Hz, 1H), 4.35 (t, J=6.9 Hz, 2H), 3.46 (t, J=5.6 Hz, 2H), 3.2-2.7 (m, 2H), 3.15 (s, 3H), 2.90 (s, 3H), 2.57 (s, 3H), 2.37-2.06 (m, 2H), 2.02-1.88 (m, 2H) ppm. (OH was not observed)

MS (ESI) m/z: 412 (M+H)$^+$.

Example 9

8-(4-Fluorophenyl)-1-(isoxazol-3-ylmethyl)-N,N,2-trimethyl-1,6,7,8-tetrahydrochromeno[7,8-d]imidazole-5-carboxamide

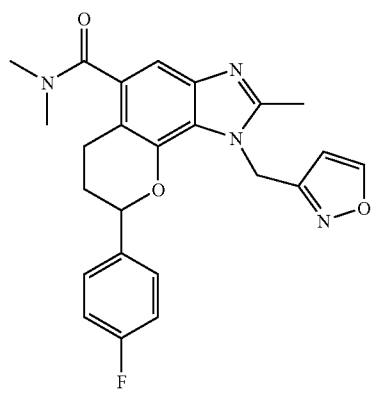 [SMILES: Cc1nc2cc(C(=O)N(C)C)c3c(c2n1Cc1ccon1)OC(c1ccc(F)cc1)CC3]

STEP 1: 3-(Bromomethyl)isoxazole

To a solution of isoxazol-3-ylmethanol (100 mg, 1.01 mmol, EP87953) in dichloromethane (10 mL) was added phosphorus tribromide (820 mg, 3.03 mmol) at 0° C. The mixture was stirred at room temperature for 3 hours. The reaction was quenched by saturated sodium hydrogencarbonate aqueous solution. The mixture was extracted twice with dichloromethane. The combined organic layer was dried over sodium sulfate and concentrated with N,N-dimethylformamide (1.0 mL) in vacuo to afford the title compound as a N,N-dimethylformamide solution.

STEP 2: 8-(4-Fluorophenyl)-1-(isoxazol-3-ylmethyl)-N,N,2-trimethyl-1,6,7,8-tetrahydrochromeno[7,8-d]imidazole-5-carboxamide To a solution of 8-(4-fluorophenyl)-N,N,2-trimethyl-3,6,7,8-tetrahydrochromeno[7,8-d]imidazole-5-carboxamide (50.0 mg, 0.141 mmol, Step 8 of Example 8) in N,N-dimethylformamide (1.4 mL), was added sodium hydride (6.7 mg, 0.17 mmol) at 0° C. and the mixture was stirred at 0° C. for 30 minutes. Then a solution of 3-(bromomethyl)isoxazole in N,N-dimethylformamide (1.0 mL, Step 1) was added to the mixture at 0° C. The mixture was allowed to warm to room temperature, stirred for 4 hours and left at the same temperature overnight. The reaction was quenched by saturated ammonium chloride aqueous solution. The mixture was extracted twice with ethyl acetate. The combined organic layer was washed with water and brine, dried over sodium sulfate, and concentrated in vacuo. The residue was purified by preparative TLC eluting with hexane/ethyl acetate (1:1, twice), then dichloromethane/methanol (20:1, twice) to afford the title compound as a pale yellow solid (23.5 mg, 38%).

$^1$H NMR (CDCl$_3$, 270 MHz) δ: 8.31 (d, J=1.5 Hz, 2H), 7.31 (dd, J=8.8, 5.1 Hz, 2H), 7.17 (s, 1H), 7.06 (dd, J=8.4, 8.4 Hz, 1H), 6.03 (d, J=1.5 Hz, 1H), 5.66 (d, J=16.1 Hz, 1H), 5.57 (d, J=16.1 Hz, 1H), 5.13 (dd, J=10.3, 2.2 Hz, 1H), 3.2-2.7 (m, 2H), 3.16 (s, 3H), 2.91 (s, 3H), 2.57 (s, 3H), 2.35-2.02 (m, 2H) ppm.

MS (ESI) m/z: 435 (M+H)$^+$.

Example 10

N,N-Di[$^2$H$_3$]methyl-1-(2-methoxyethyl)-2-methyl-8-phenyl-1,6,7,8-tetrahydrochromeno[7,8-d]imidazole-5-carboxamide

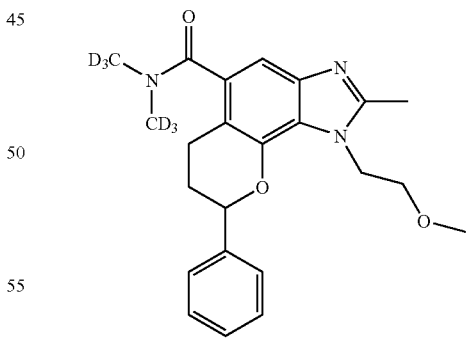

A mixture of 1-(2-methoxyethyl)-2-methyl-8-phenyl-1,6,7,8-tetrahydrochromeno[7,8-d]imidazole-5-carboxylic acid (200 mg, 0.55 mmol, Step 12 of Example 1), N,N-di[$^2$H$_3$]methylamine hydrochloride (96 mg, 1.09 mmol), N,N-diisopropylethylamine (0.38 mL, 2.18 mmol), 1-[3-(dimethylamino)propyl]-3-ethylcarbodiimide hydrochloride (157 mg, 0.82 mmol), and 1-hydroxybenzotriazole hydrate (125 mg, 0.82 mmol) in 1-methyl-2-pyrrolidinone (3 mL) was stirred at room temperature for 8 hours. Then, the mixture was poured onto water (30 mL), and the aqueous layer was extracted with ethyl acetate. The combined organic layer was dried over magnesium sulfate and concentrated in vacuo. The residue was purified by column chromatography on NH-gel eluting with dichloromethane/methanol (20:1) to afford the title compound as a white amorphous (175 mg, 80%).

$^1$H NMR (CDCl$_3$, 300 MHz) δ: 7.44-7.34 (m, 5H), 7.13 (s, 1H), 5.15 (dd, J=2.6 and 10.6 Hz, 1H), 4.50-4.35 (m, 2H), 3.68-3.56 (m, 2H), 3.2-2.7 (m, 2H), 3.18 (s, 3H), 2.57 (s, 3H), 2.35-2.10 (m, 2H).

MS (ESI) m/z: 400 (M+H)$^+$.

Example 11

8-(2,4-Difluorophenyl)-N-(2-hydroxyethyl)-1-(2-methoxyethyl)-N,2-dimethyl-1,6,7,8-tetrahydro-chromeno[7,8-d]imidazole-5-carboxamide

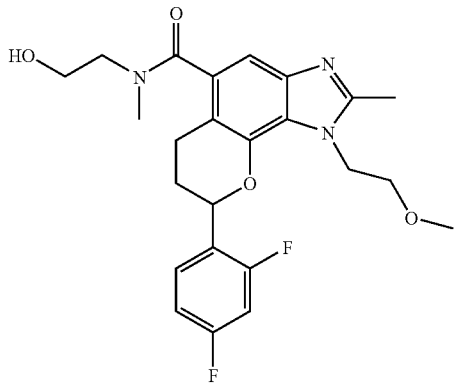 [SMILES: COCCn1c(C)nc2cc(C(=O)N(C)CCO)c3c(c21)OC(c1ccc(F)cc1F)CC3]

STEP 1: 7-(Benzyloxy)-N-(2-hydroxyethyl)-1-(2-methoxyethyl)-N,2-dimethyl-1H-benzimidazole-5-carboxamide The title compound was prepared as a white amorphous in 99% yield from 7-(benzyloxy)-1-(2-methoxyethyl)-2-methyl-1H-benzimidazole-5-carboxylic acid (5.00 g, 14.7 mmol, Step 5 of Example 1) and 2-(methylamino)ethanol (1.21 g, 16.2 mmol) by the same manner in Step 13 of Example 1.

$^1$H NMR (CDCl$_3$, 270 MHz) δ: 7.43-7.39 (m, 6H), 6.97 (bs, 1H), 5.20 (s, 2H), 4.45 (t, J=5.1 Hz, 2H), 3.98-3.81 (m, 2H), 3.81-3.75 (m, 2H), 3.61 (t, J=5.1 Hz, 2H), 3.18 (s, 3H), 3.12 (s, 3H), 2.60 (s, 3H) ppm. (OH was not observed)

MS (ESI) m/z: 398 (M+H)$^+$.

STEP 2: 7-Hydroxy-N-(2-hydroxyethyl)-1-(2-methoxyethyl)-N,2-dimethyl-1H-benzimidazole-5-carboxamide The title compound was prepared as a yellow oil in quantitative yield from 7-(benzyloxy)-N-(2-hydroxyethyl)-1-(2-methoxyethyl)-N,2-dimethyl-1H-benzimidazole-5-carboxamide (1.15 g, 2.89 mmol, Step 1) by the same manner in Step 7 of Example 1.

$^1$H NMR (DMSO-d$_6$, 270 MHz) δ: 7.50-6.99 (m, 1H), 6.81 (s, 1H), 4.61-4.31 (m, 2H), 4.04-3.37 (m, 6H), 3.27 (s, 3H), 3.09 (s, 3H), 2.58 (s, 3H) ppm. (2×OH were not observed)

MS (ESI) m/z: 308 (M+H)$^+$

STEP 3: 6-[(Dimethylamino)methyl]-7-hydroxy-N-(2-hydroxyethyl)-1-(2-methoxyethyl)-N,2-dimethyl-1H-benzimidazole-5-carboxamide The title compound was prepared as a colorless oil in 45% yield from 7-hydroxy-N-(2-hydroxyethyl)-1-(2-methoxyethyl)-N,2-dimethyl-1H-benzimidazole-5-carboxamide (500 mg, 1.63 mmol, Step 2) by the same manner in Step 3 of Example 5.

$^1$H NMR (CDCl$_3$, 270 MHz) δ: 6.99 (s, 1H), 4.61-4.43 (m, 2H), 4.43-3.54 (m, 9H), 3.28 (s, 3H), 2.94 (s, 2H), 2.58 (s, 3H), 2.36 (s, 6H) ppm. (2×OH were not observed)

MS (ESI) m/z: 365 (M+H)$^+$. 363 (M−H)$^-$.

STEP 4: 1-[1-(2,4-Difluorophenyl)vinyl]pyrrolidine

To a solution of 1-(2,4-difluorophenyl)ethanone (10.0 g, 64.0 mmol) and pyrrolidine (32.1 mL, 384 mmol) in hexane (150 mL) was added titanium tetrachloride (3.86 mL, 35.2 mmol) dropwise at 0° C. over 15 minutes. The reaction mixture was stirred at room temperature for 24 hours and filtered. The filtrate was evaporated in vacuo to give pale yellow oil, which was distilled under reduced pressure (0.3 mmHg, 90-120° C.) to give the title compound as a pale yellow oil (4.90 g, 36%).

$^1$H NMR (CDCl$_3$, 300 MHz) δ: 7.33-7.25 (m, 1H), 6.91-6.76 (m, 2H), 3.81 (s, 1H), 3.68 (s, 1H), 3.11-2.98 (m, 4H), 1.92-1.78 (m, 4H) ppm.

STEP 5: 6-[3-(2,4-Difluorophenyl)-3-oxopropyl]-7-hydroxy-N-(2-hydroxyethyl)-1-(2-methoxyethyl)-N,2-dimethyl-1H-benzimidazole-5-carboxamide The title compound was prepared as a white solid in 40% yield from 6-[(dimethylamino)methyl]-7-hydroxy-N-(2-hydroxyethyl)-1-(2-methoxyethyl)-N,2-dimethyl-1H-benzimidazole-5-carboxamide (1.16 g, 3.19 mmol, Step 3) and 1-[1-(2,4-difluorophenyl)vinyl]pyrrolidine (1.00 g, 4.78 mmol, Step 4) by the same manner in Step 9 of Example 1.

$^1$H NMR (CDCl$_3$, 270 MHz) δ: 9.10 (br s, 1H, OH), 7.96 (q, J=8.1 Hz, 1H), 7.07 (s, 1H), 7.02-6.74 (m, 2H), 4.67-4.42 (m, 2H), 4.03-3.80 (m, 8H), 3.31 (s, 3H), 2.92 (s, 3H), 2.59 (s, 3H) ppm. (CH$_2$ and OH were not observed)

MS (ESI) m/z: 476 (M+H)$^+$, 474 (M−H)$^-$.

STEP 6: 6-[3-(2,4-Difluorophenyl)-3-hydroxypropyl]-7-hydroxy-N-(2-hydroxyethyl)-1-(2-methoxyethyl)-N,2-dimethyl-1H-benzimidazole-5-carboxamide The title compound was prepared as a white solid in quantitative yield from 6-[3-(2,4-difluorophenyl)-3-oxopropyl]-7-hydroxy-N-(2-hydroxyethyl)-1-(2-methoxyethyl)-N,2-dimethyl-1H-benzimidazole-5-carboxamide (617 mg, 1.30 mmol, Step 5) by the same manner in Step 10 of Example 1.

$^1$H NMR (CDCl$_3$, 270 MHz) δ: 7.67-7.38 (m, 1H), 7.12 (s, 1H), 6.95-6.47 (m, 2H), 4.99-4.70 (m, 1H), 4.70-4.29 (m, 2H), 4.07-3.88 (m, 2H), 4.07-2.80 (m, 8H), 3.42 (s, 3H), 2.92 (s, 3H), 2.57 (s, 3H) ppm. (3×OH were not observed)

MS (ESI) m/z: 478 (M+H)$^+$, 476 (M−H)$^-$.

STEP 7: 8-(2,4-Difluorophenyl)-N-(2-hydroxyethyl)-1-(2-methoxyethyl)-N,2-dimethyl-1,6,7,8-tetrahydrochromeno[7,8-d]imidazole-5-carboxamide The title compound was prepared as a white solid in 64% yield from 6-[3-(2,4-difluorophenyl)-3-hydroxypropyl]-7- hydroxy-N-(2-hydroxyethyl)-1-(2-methoxyethyl)-N,2-dimethyl-1H-benzimidazole-5-carboxamide (640 mg, 0.21 mmol, Step 6) by the same manner in Step 11 of Example 1.

$^1$H NMR (CDCl$_3$, 270 MHz) δ: 9.72 (s, 1H), 8.03 (d, J=7.2 Hz, 2H), 7.95 (s, 1H), 7.59 (t, J=7.9 Hz, 1H), 7.46 (t, J=7.9 Hz, 2H), 4.61 (t, J=5.3 Hz, 2H), 3.92 (s, 3H), 3.83-3.73 (m, 4H), 3.41 (t, J=5.3 Hz, 2H), 3.29 (s, 3H), 2.60 (s, 3H) ppm.

MS (ESI) m/z: 460 (M+H)$^+$.

Example 12

(−)-8-(2,4-Difluorophenyl)-N-(2-hydroxyethyl)-1-(2-methoxyethyl)-N,2-dimethyl-1,6,7,8-tetrahydrochromeno[7,8-d]imidazole-5-carboxamide and

Example 13

(+)-8-(2,4-Difluorophenyl)-N-(2-hydroxyethyl)-1-(2-methoxyethyl)-N,2-dimethyl-1,6,7,8-tetrahydrochromeno[7,8-d]imidazole-5-carboxamide The fraction-1 (158 mg) and fraction-2 (148 mg) were prepared from racemic 8-(2,4-difluorophenyl)-N-(2-hydroxyethyl)-1-(2-methoxyethyl)-N,2-dimethyl-1,6,7,8-tetrahydrochromeno[7,8-d]imidazole-5-carboxamide (356 mg, STEP 7 in Example 11) by chiral SFC as follows.

Isolation Condition
  Apparatus: Berger MultiGram II™ (Mettler-Toledo)
  Column: DAICEL CHIRALPAK AD-H (20 mm×250 mm, DAICEL)
  Column temperature: 35° C.
  Outlet pressure: 100 bar
  Mobile phase: CO2/0.1% Diethylamine in 2-Propanol (80/20)
  Flow rate: 40 mL/min (−)-8-(2,4-Difluorophenyl)-N-(2-hydroxyethyl)-1-(2-methoxyethyl)-N,2-dimethyl-1,6,7,8-tetrahydrochromeno[7,8-d]imidazole-5-carboxamide (fraction-1)

$^1$H NMR: spectrum data were identical with those of the racemate
  optical rotation: $[\alpha]_D^{21}$=−22.9° (c=0.21, Methanol)
  retention time: 10 min (+)-8-(2,4-Difluorophenyl)-N-(2-hydroxyethyl)-1-(2-methoxyethyl)-N,2-dimethyl-1,6,7,8-tetrahydrochromeno[7,8-d]imidazole-5-carboxamide (fraction-2)

$^1$H NMR: spectrum data were identical with those of the racemate
  optical rotation: $[\alpha]_D^{21}$=+24.8° (c=0.23, Methanol)
  retention time: 12 min Following Examples 14 and 15 were prepared from 1-(2-methoxyethyl)-2-methyl-8-phenyl-1,6,7,8-tetrahydrochromeno[7,8-d]imidazole-5-carboxylic acid (Step 12 of Example 1) and corresponding various amines according to the procedure described in Step 13 of Example 1.

| Example 14 | 5-[(3-Fluoroazetidin-1-yl)carbonyl]-1-(2-methoxyethyl)-2-methyl-8-phenyl-1,6,7,8-tetrahydrochromeno[7,8-d]imidazole |
|---|---|
| 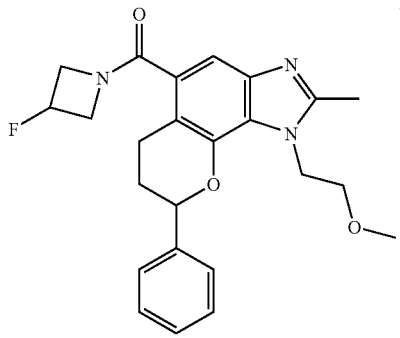 [SMILES: COCCn1c(C)nc2cc(C(=O)N3CC(F)C3)c3c(c21)OC(c1ccccc1)CC3] | White solid<br>$^1$H NMR (CDCl$_3$, 300 MHz) δ : 7.51-7.33 (m, 5H), 7.22 (s, 1H), 5.33 (br d, J = 56.5 Hz, 1H), 5.15 (dd, J = 11.0, 2.2 Hz, 1H), 4.58-4.02 (m, 6H), 3.66-3.57 (m, 2H), 3.22-2.97 (m, 2H), 3.18 (s, 3H), 2.58 (s, 3H), 2.33-2.22 (m, 1H), 2.20-2.04 (m, 1H) ppm.<br>MS (ESI) m/z: 424 (M + H)$^+$. |
| Example 15 | 5-(Azetidin-1-ylcarbonyl)-1-(2-methoxyethyl)-2-methyl-8-phenyl-1,6,7,8-tetrahydrochromeno[7,8-d]imidazole |
| 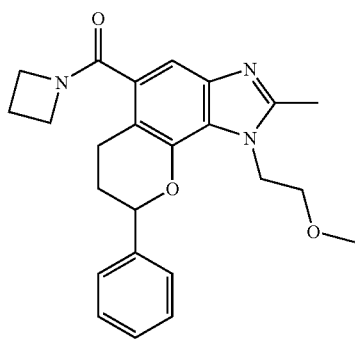 [SMILES: COCCn1c(C)nc2cc(C(=O)N3CCC3)c3c(c21)OC(c1ccccc1)CC3] | White solid<br>$^1$H NMR (CDCl$_3$, 300 MHz) δ : 7.50-7.32 (m, 5H), 7.21 (s, 1H), 5.15 (dd, J = 11.0, 2.2 Hz, 1H), 4.49-4.39 (m, 2H), 4.29-3.93 (m, 4H), 3.66-3.58 (m, 2H), 3.26-2.95 (m, 2H), 3.17 (s, 3H), 2.57 (s, 3H), 2.38-2.25 (m, 3H), 2.18-2.04 (m, 1H) ppm.<br>MS (ESI) m/z: 406 (M + H)$^+$. |

Example 16

(−)-5-(Azetidin-1-ylcarbonyl)-1-(2-methoxyethyl)-2-methyl-8-phenyl-1,6,7,8-tetrahydrochromeno[7,8-d]imidazole and

Example 17

(+)-5-(Azetidin-1-ylcarbonyl)-1-(2-methoxyethyl)-2-methyl-8-phenyl-1,6,7,8-tetrahydrochromeno[7,8-d]imidazole The fraction-1 (86 mg) and fraction-2 (82 mg) were prepared from racemic 5-(azetidin-1-ylcarbonyl)-1-(2-methoxyethyl)-2-methyl-8-phenyl-1,6,7,8-tetrahydrochromeno[7,8-d]imidazole (230 mg, Example 15) by HPLC as follows.

Isolation Condition
Column: CHIRALCEL OD-H (20 mm×250 mm, DAICEL)
Mobile phase: n-Hexane/Ethanol/Diethylamine (85/15/0.1)
Flow rate: 20 mL/min (−)-5-(Azetidin-1-ylcarbonyl)-1-(2-methoxyethyl)-2-methyl-8-phenyl-1,6,7,8-tetrahydrochromeno[7,8-d]imidazole (fraction-1)

$^1$H NMR: spectrum data were identical with those of the racemate
optical rotation: $[\alpha]_D^{21}=-23.5°$ (c=0.21, Methanol)
retention time: 15.7 min (+)-5-(Azetidin-1-ylcarbonyl)-1-(2-methoxyethyl)-2-methyl-8-phenyl-1,6,7,8-tetrahydrochromeno[7,8-d]imidazole (fraction-2)

$^1$H NMR: spectrum data were identical with those of the racemate
optical rotation: $[\alpha]_D^{21}=+25.0°$ (c=0.20, Methanol)
retention time: 21.7 min All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications could be made without departing from the spirit of the invention.

The invention claimed is:
1. A compound of the formula (I):

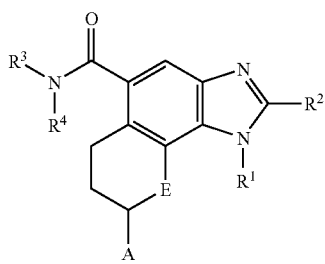

(I)

or a pharmaceutically acceptable salt thereof, wherein;

$R^1$ represents a $C_1$-$C_6$ alkyl group being substituted with 1 to 2 substituents independently selected from the group consisting of a hydroxy group, a $C_1$-$C_6$ alkoxy group, a hydroxy-substituted $C_3$-$C_7$ cycloalkyl group, a hydroxy-$C_1$-$C_6$ alkyl-substituted $C_3$-$C_7$ cycloalkyl group, an aryl group, a hydroxy-substituted aryl group, a heteroaryl group and a halogen-substituted heteroaryl group;

$R^2$ represents a hydrogen atom or a $C_1$-$C_6$ alkyl group being unsubstituted or substituted with 1 to 2 substituents independently selected from the group consisting of a hydroxy group and a $C_1$-$C_6$ alkoxy group;

$R^3$ and $R^4$ independently represent a hydrogen atom, or a $C_1$-$C_6$ alkyl, $C_3$-$C_7$ cycloalkyl or heteroaryl group being unsubstituted or substituted with 1 to 3 substituents independently selected from the group consisting of a deuterium, a halogen atom, a hydroxy group, a $C_1$-$C_6$ alkoxy group and a $C_3$-$C_7$ cycloalkyl group; or $R^3$ and $R^4$ taken together with the nitrogen atom to which they are attached form a 4 to 6 membered heterocyclic group being unsubstituted or substituted with 1 to 2 substituents selected from the group consisting of a hydroxy group, an oxo group, a $C_1$-$C_6$ alkyl group, a $C_1$-$C_6$ acyl group, and a hydroxy-$C_1$-$C_6$ alkyl group;

A represents an aryl or heteroaryl group being unsubstituted or substituted with 1 to 5 substituents independently selected from the group consisting of a halogen atom, a $C_1$-$C_6$ alkyl group, a hydroxy-$C_1$-$C_6$ alkyl group, a $C_1$-$C_6$ alkoxy-substituted $C_1$-$C_6$ alkyl group, —NR$^5$SO$_2$R$^6$ and —CONR$^7$R$^8$;

$R^5$, $R^7$ and $R^8$ independently represent a hydrogen atom or a $C_1$-$C_6$ alkyl group;

$R^6$ represents a $C_1$-$C_6$ alkyl group; and

E represents an oxygen atom or NH.

2. The compound or the pharmaceutically acceptable salt, as claimed in claim 1, wherein $R^1$ is a $C_1$-$C_6$ alkyl group being substituted with 1 to 2 substituents independently selected from the group consisting of a hydroxy group, a $C_1$-$C_6$ alkoxy group and a heteroaryl group;

$R^2$ is a $C_1$-$C_6$ alkyl group;

$R^3$ and $R^4$ are independently a hydrogen atom or a $C_1$-$C_6$ alkyl being unsubstituted or substituted with 1 to 3 substituents independently selected from the group consisting of a deuterium, a hydroxy group and a $C_1$-$C_6$ alkoxy group; or $R^3$ and $R^4$ taken together with the nitrogen atom to which they are attached form a 4 to 6 membered heterocyclic group being unsubstituted or substituted with 1 to 2 substituent selected from the group consisting of a hydroxy group, an oxo group, a $C_1$-$C_6$ alkyl group, a $C_1$-$C_6$ acyl group and a hydroxy-$C_1$-$C_6$ alkyl group;

A is an aryl group being unsubstituted or substituted with 1 to 5 substituents independently selected from the group consisting of a halogen atom, a $C_1$-$C_6$ alkyl group, a hydroxy-$C_1$-$C_6$ alkyl group, a $C_1$-$C_6$ alkoxy-substituted $C_1$-$C_6$ alkyl group, —NR$^5$SO$_2$R$^6$ and —CONR$^7$R$^8$;

$R^5$, $R^7$ and $R^8$ are independently a hydrogen atom or a $C_1$-$C_6$ alkyl group; and $R^6$ is a $C_1$-$C_6$ alkyl group; and E is an oxygen atom.

3. The compound or the pharmaceutically acceptable salt, as claimed in claim 1, wherein $R^1$ is a $C_1$-$C_6$ alkyl group being substituted with a hydroxy group, a $C_1$-$C_6$ alkoxy group or a heteroaryl group;

$R^2$ is a $C_1$-$C_6$ alkyl group;

$R^3$ and $R^4$ are independently a hydrogen atom, a methyl group, —CD$_3$ or 2-hydroxyethyl group; or $R^3$ and $R^4$ taken together with the nitrogen atom to which they are attached form a morpholino group;

A is an aryl group being unsubstituted or substituted with a halogen atom; and

E is an oxygen atom.

4. The compound of claim 1, which is selected from:

(−)-1-(2-methoxyethyl)-N,N,2-trimethyl-8-phenyl-1,6,7,8-tetrahydrochromeno[7,8-d]imidazole-5-carboxamide;

(−)-8-(4-fluorophenyl)-1-(2-methoxyethyl)-N,N,2-trimethyl-1,6,7,8-tetrahydrochromeno[7,8-d]imidazole-5-carboxamide;

8-(4-fluorophenyl)-1-(3-hydroxypropyl)-N,N,2-trimethyl-1,6,7,8-tetrahydrochromeno [7,8-d]imidazole-5-carboxamide;

8-(4-fluorophenyl)-1-(isoxazol-3-ylmethyl)-N,N,2-trimethyl-1,6,7,8-tetrahydrochromeno[7,8-d]imidazole-5-carboxamide;

N,N-di[$^2$H$_3$]methyl-1-(2-methoxyethyl)-2-methyl-8-phenyl-1,6,7,8-tetrahydrochromeno[7,8-d]imidazole-5-carboxamide;

8-(4-fluorophenyl)-N-(2-hydroxyethyl)-1-(2-methoxyethyl)-N,2-dimethyl-1,6,7,8-tetrahydrochromeno[8,7-d]imidazole-5-carboxamide;

(8-(4-fluorophenyl)-1-(2-methoxyethyl)-2-methyl-1,6,7,8-tetrahydrochromeno[8,7-d]imidazol-5-yl)(morpholino)methanone;

or a pharmaceutically acceptable salt thereof.

5. A pharmaceutical composition comprising the compound or the pharmaceutically acceptable salt thereof, as claimed in claim 1, and a pharmaceutically acceptable carrier.

6. The pharmaceutical composition as claimed in claim 5 further comprising other pharmacologically active agent(s).

7. A method for the treatment of a condition mediated by acid pump inhibitory activity in a mammalian subject including a human, which comprises administering to a mammal in need of such treatment a therapeutically effective amount of the compound or the pharmaceutically acceptable salt thereof, as claimed in claim 1.

8. The method as claimed in claim 7, wherein said condition is gastrointestinal disease, gastroesophageal disease, gastroesophageal reflux disease (GERD), laryngopharyngeal reflux disease, peptic ulcer, gastric ulcer, duodenal ulcer, NSAID-induced ulcers, gastritis, infection of *Helicobacter pylori*, dyspepsia, functional dyspepsia, Zollinger-Ellison syndrome, non-erosive reflux disease (NERD), visceral pain, cancer, heartburn, nausea, esophagitis, dysphagia, hypersalivation, airway disorders or asthma.

* * * * *

UNITED STATES PATENT AND TRADEMARK OFFICE
CERTIFICATE OF CORRECTION

PATENT NO. : 8,466,166 B2  
APPLICATION NO. : 12/442277  
DATED : June 18, 2013  
INVENTOR(S) : Koike et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 505 days.

Signed and Sealed this  
Eighth Day of September, 2015

Michelle K. Lee  
*Director of the United States Patent and Trademark Office*